US010494361B2

(12) United States Patent
Atwood

(10) Patent No.: US 10,494,361 B2
(45) Date of Patent: *Dec. 3, 2019

(54) CRYSTALLINE 4-AMINO-2-(2,6-DIOXOPIPERIDINE-3-YL)ISOINDOLINE-1,3-DIONE DIHYDRATE, COMPOSITIONS AND METHODS OF USE THEREOF

(71) Applicant: Celgene Corporation, Summit, NJ (US)

(72) Inventor: Jerry Lee Atwood, Columbia, MO (US)

(73) Assignee: Celgene Corporation, Summit, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/124,066

(22) Filed: Sep. 6, 2018

(65) Prior Publication Data

US 2019/0071414 A1  Mar. 7, 2019

Related U.S. Application Data

(63) Continuation of application No. 15/849,285, filed on Dec. 20, 2017, now Pat. No. 10,093,647.

(60) Provisional application No. 62/511,878, filed on May 26, 2017.

(51) Int. Cl.
*C07D 401/04* (2006.01)
*A61K 31/4035* (2006.01)
*A61K 31/45* (2006.01)

(52) U.S. Cl.
CPC ........ *C07D 401/04* (2013.01); *A61K 31/4035* (2013.01); *A61K 31/45* (2013.01); *C07B 2200/13* (2013.01)

(58) Field of Classification Search
CPC .................................................. C07D 401/04
USPC ........................................ 546/200; 514/323
See application file for complete search history.

(56) References Cited

U.S. PATENT DOCUMENTS

| | | | |
|---|---|---|---|
| 4,551,177 A | 11/1985 | Trubiano et al. | |
| 5,385,901 A | 1/1995 | Kaplan et al. | |
| 5,593,696 A | 1/1997 | McNally et al. | |
| 5,594,637 A | 1/1997 | Eisenberg et al. | |
| 5,619,991 A | 4/1997 | Sloane | |
| 5,635,517 A | 6/1997 | Muller et al. | |
| 5,712,291 A | 1/1998 | D'Amato | |
| 5,731,325 A | 3/1998 | Andrulis, Jr. et al. | |
| 5,798,368 A | 8/1998 | Muller et al. | |
| 5,832,449 A | 11/1998 | Cunningham | |
| 5,882,656 A | 3/1999 | Bechard et al. | |
| 5,974,203 A | 10/1999 | Tadokoro et al. | |
| 6,045,501 A | 4/2000 | Elsayed et al. | |
| 6,055,507 A | 4/2000 | Cunningham | |
| 6,063,026 A | 5/2000 | Schauss et al. | |
| 6,131,090 A | 10/2000 | Basso et al. | |
| 6,202,923 B1 | 3/2001 | Boyer et al. | |
| 6,281,230 B1 | 8/2001 | Muller et al. | |
| 6,315,720 B1 | 11/2001 | Williams et al. | |
| 6,316,471 B1 | 11/2001 | Muller et al. | |
| 6,335,349 B1 | 1/2002 | Muller et al. | |
| 6,476,052 B1 | 11/2002 | Muller et al. | |
| 6,555,554 B2 | 4/2003 | Muller et al. | |
| 6,561,976 B2 | 5/2003 | Elsayed et al. | |
| 6,561,977 B2 | 5/2003 | Williams et al. | |
| 6,627,646 B2* | 9/2003 | Bakale | C07D 401/12 514/303 |
| 6,755,784 B2 | 6/2004 | Williams et al. | |
| 6,878,733 B1 | 4/2005 | Shenoy et al. | |
| 6,896,399 B2 | 5/2005 | Nomura et al. | |
| 6,908,432 B2 | 6/2005 | Elsayed et al. | |
| 7,041,680 B2 | 5/2006 | Muller et al. | |
| 7,119,106 B2 | 10/2006 | Muller et al. | |
| 7,189,740 B2 | 3/2007 | Zeldis | |
| 7,393,862 B2 | 7/2008 | Zeldis | |
| 7,393,863 B2 | 7/2008 | Zeldis | |
| 7,465,800 B2 | 12/2008 | Jaworsky et al. | |
| 7,629,360 B2 | 12/2009 | Muller et al. | |
| 7,709,031 B2 | 5/2010 | Greenway et al. | |
| 7,709,502 B2 | 5/2010 | Muller et al. | |
| 7,855,217 B2 | 12/2010 | Jaworski et al. | |
| 7,863,297 B2 | 1/2011 | Zeldis | |
| 7,959,566 B2 | 6/2011 | Williams et al. | |
| 7,968,569 B2 | 6/2011 | Zeldis | |
| 7,994,327 B2 | 8/2011 | Ge et al. | |
| 8,158,653 B2 | 4/2012 | Muller et al. | |
| 8,188,118 B2 | 5/2012 | Zeldis | |
| 8,198,262 B2 | 6/2012 | Zeldis | |
| 8,198,306 B2 | 6/2012 | Zeldis | |

(Continued)

FOREIGN PATENT DOCUMENTS

WO    WO 96/13790 A1    5/1996
WO    WO 98/03502 A1    1/1998

(Continued)

OTHER PUBLICATIONS

Bernstein, "Polymorphism in . . . " p. 115-118, 272. (Year: 2002).*
Davidovich et al., "Detection of polymorphism . . . " Am. Pharm. Rev. 7(1) p. 10, 12, 14, 16, 100.. (Year: 2004).*
Dean "Analytical Chem . . . " p. 10.24-10.26. (Year: 1995).*
Ivanisevic et al. "Use of X-ray . . . " Pharm. Sci. Encycl. p. 1-42.. (Year: 2010).*
Seddon "Pseudopolymorph . . . " Crystal Growth &amp; design v.4(6) p. 1087 (2 pages from internet). (Year: 2004).*

(Continued)

*Primary Examiner* — Patricia L Morris
(74) *Attorney, Agent, or Firm* — Jones Day

(57) ABSTRACT

Provided herein is a crystalline 4-amino-2-(2,6-dioxopiperidine-3-yl)isoindoline-1,3-dione dihydrate. Pharmaceutical compositions comprising the crystalline 4-amino-2-(2,6-dioxopiperidine-3-yl)isoindoline-1,3-dione dihydrate are also disclosed.

12 Claims, 6 Drawing Sheets

(56) References Cited

U.S. PATENT DOCUMENTS

| | | | |
|---|---|---|---|
| 8,204,763 | B2 | 6/2012 | Elsayed et al. |
| 8,207,200 | B2 | 6/2012 | Zeldis |
| 8,315,886 | B2 | 11/2012 | Williams et al. |
| 8,530,498 | B1 | 9/2013 | Zeldis |
| 8,589,188 | B2 | 11/2013 | Elsayed et al. |
| 8,626,531 | B2 | 1/2014 | Williams et al. |
| 8,648,095 | B2 | 2/2014 | Zeldis |
| 8,673,939 | B2 | 3/2014 | Zeldis |
| 8,722,647 | B2 | 5/2014 | Zeldis |
| 8,735,428 | B2 | 5/2014 | Zeldis |
| 8,759,375 | B2 | 6/2014 | Zeldis |
| 8,828,427 | B2 * | 9/2014 | Tutino ................. A61K 9/4858 424/452 |
| 9,101,621 | B2 | 8/2015 | Zeldis |
| 9,101,622 | B2 | 8/2015 | Zeldis |
| 9,695,146 | B2 * | 7/2017 | Stahly ................. C07D 401/04 |
| 10,093,647 | B1 * | 10/2018 | Atwood ............... C07D 401/04 |
| 2002/0054899 | A1 | 5/2002 | Zeldis et al. |
| 2007/0155791 | A1 | 7/2007 | Zeldis et al. |
| 2008/0051431 | A1 | 2/2008 | Verhelle et al. |
| 2017/0258778 | A1 | 9/2017 | Stahly et al. |

FOREIGN PATENT DOCUMENTS

| | | |
|---|---|---|
| WO | WO 98/13783 A1 | 4/1998 |
| WO | WO 99/10829 A1 | 3/1999 |
| WO | WO 00/51053 A1 | 8/2000 |
| WO | WO 02/43720 A2 | 6/2002 |
| WO | WO 02/59106 A1 | 8/2002 |
| WO | WO 02/064083 A2 | 8/2002 |
| WO | WO 2011/050962 A1 | 5/2011 |
| WO | WO 2013/012485 A2 | 1/2013 |
| WO | WO 2013/126326 A1 | 8/2013 |
| WO | WO 2014/160690 A1 | 10/2014 |
| WO | WO 2018/013689 A1 | 1/2018 |

OTHER PUBLICATIONS

Rodriguez-Spong et al., "General principles, etc.," Adv. Drug Delivery Reviews 56 241-274. (Year: 2004).*
Kirk-Othmer Encyclopedia of Chemical Technology, 8, pp. 95-147. (Year: 2002).*
Vippagunta et al., "Crystalline Solids", Advanced Drug Delivery Reviews 48 .3-26. (Year: 2001).*
Guillory (in Brittain ed.), "Polymorphism in Pharmaceutical Solids.," NY: Marcel Dekker, Inc., 1-2, 183-226. (Year: 1999).*
Braga et al., "Making crystals from . . . " J. Royal Soc. Chem. Commun. p. 3635-3645. (Year: 2005).*
CMU Pharmaceutical polymorphism, internet p. 1-3 printout Apr. 3, 2008. (Year: 2002).*
Singhal et al., "Drug Polymorphism, etc.," Advanced Drug Delivery reviews 56, p. 335-347. (Year: 2004).*
Concise Encyclopedia Chemistry, NY: Walter de Gruyter, 872-873. (Year: 1993).*
Jain et al., "Polymorphism in Pharmacy", Indian Drugs, 23(6) 315-329. (Year: 1986).*
Muzaffar et al., "Polymorphism and Drug Availability, etc.," J of Pharm. (Lahore), 1(1), 59-66. (Year: 1979).*
U.S. Pharnnacopia #23, National Formulary #18,1843-1844. (Year: 1995).*
Doelker, english translation of S.T.P, Pratiques, 9(5), 399-409, pp. 1-33. (Year: 1999).*
Doelker, english translation of Ann. Pharm. Fr.,60: 161-176, pp. 1-39. (Year: 2002).*
Taday et al., "Using Terahertz, etc.," J of Pharm. Sci., 92(4), 831-838. (Year: 2003).*
Otuska et al., "Effect of Polymorphic, etc.," Chem. Pharm. Bull., 47(6) 852-8569. (Year: 1999).*
Nie et al., "Source analysis, etc.," CA 1743748. (Year: 2015).*
"CDC meeting: Mar. 26, 1997 minutes and agenda regarding thalidomide."

"Celgene's Revlimid an orphan drug, says FDA," Marketletter Oct. 15, 2001.
"Center for drug evaluation and research approval package for: Application No. 18-662/S-038," (2000).
"Center for drug evaluation and research approval package for: Application No. NDA 20-785 approval letter(s)," Sep. 19, 1997 and Jul. 16, 1998.
"Celgene drug promises activity in solid tumors," Markletter Jun. 18, 2001.
"Center for drug evaluation and research, Application No. 204026Orig1s000," Pharmacolgy Review(s), dated Dec. 13, 2012. [retrieved on Oct. 29, 2016]. Retrieved from the internet: <http://www.accessdata.fda.gov/drugsatfda_docs/nda/2013/204026Orig1s000PharmR.pdf>.
"Center for Drug Evaluation and Research, Approval Package for: Application No. 14-691/S-020," ALKERAN® (melphalan) Tablets, product information, GlaxoSmithKline (2001).
"EntreMed moves towards commercialization with production of thalidomide analogs; Next generation drug candidates to be manufactured in preparation for clinical studies," PR Newswire (2001).
Adams et al., "Proteasome inhibitors: A novel class of potent and effective antitumor agents," Cancer Res. 59:2615-2622 (1999).
Adjei et al., "A phase I trial of the farnesyl transferase inhibitor SCH66336: evidence for biological and clinical activity," Cancer Res., 60:1871-1877 (2000).
Alder et al., "The return of thaliomide—A shunned compound makes a scientific comeback," Science News 146:424-425 (1994).
Alexanian et al., "High-dose glucocorticoid treatment of resistant myeloma," Ann. Intern. Med. 105:8-11 (1986).
Alexanian et al., "Consolidation therapy of multiple myeloma with thalidomide-dexamethasone after intensive chemotherapy," Ann Oncol. 13:1116-1119 (2002).
Anderson et al., "Multiple myeloma: New insights and therapeutic approaches," Hematology Am. Soc. Hematol. Educ. Program 2000:147-165 (2000).
Anderson et al., "Novel biologically based therapies for myeloma," VIII the International Myeloma Workshop, Banff, Alberta, Canada, May 4-8, 2001; Abstract #S27.
Anderson, "The role of immunomodulatory drugs in multiple myeloma," Semin. Hematol., 40(4 Suppl. 4):23-32 (2003).
Banker ed., Modern Pharmaceutics, 3$^{rd}$ Edition, Marcel Dekker, Inc., New York, NY, pp. 451 and 596 (1996).
Barlogie et al., "Effective Treatment of Advanced Multiple Myeloma Refractory to Alkylating Agents," N. Engl. J. Med., 310(21):1353-1356 (1984).
Barlogie et al., "Thalidomide and CC-5013 in multiple myeloma: the University of Arkansas experience," Semin. Hematol., 40(4):33-38 (2003).
Barlogie et al., "Thalidomide in the management of multiple myeloma," Semin. Hematol., 38:250-259 (2001).
Beaumont et al., "Design of ester prodrugs to enhance oral absorption of poorly permeable compounds: challenges to the discovery scientist," Curr. Drug Metab., 4:461-485 (2003).
Bjorkstrand et al., "Prognostic factors in autologous stem cell transplantation for multiple myeloma: an EBMT registry study," Leuk. Lymphoma 15:265-272 (1994).
Bor, "Thalidomide shows that it can heal, too from deformer of babies to force for good," Baltimore Sun (1995).
Broder et al., "Dideoxycytidine: Current clinical experience and future prospects. A summary," Am. J. Med. 88:31S-33S (1990).
Burleson, "Review of computer applications in institutional pharmacy—1975-1981," Am. J. Hosp. Pharm. 39:53-70 (1982).
Bwire et al., Managing the teratogenic risk of thalidomide and lenalidomide: An industry perspective, Expert Opin. Drug Saf. 10:3-8 (2011).
Cairo, "Dose reductions and delays: Limitations of myelosuppressive chemotherapy," Cancer Network (2000).
Canal et al., "Benefits of pharmacological knowledge in the design and monitoring of cancer chemotherapy," Pathology Oncol. Res. 4:171-178 (1998).
Celgene assigned patents/applications indexed with pomalidomide from USPATFULL accessed Oct. 27, 2016.

(56) References Cited

OTHER PUBLICATIONS

Celgene Corporation Awarded Additional Patent Protection for Lead IMiD(TM), REVIMID(TM); Comprehensive Patent Protection for Revimid Includes Coverage of the Active Ingredient, Pharmaceutical Compositions, and Therapeutic Uses PR Newswire Aug. 28, 2001.
Celgene Corporation, "Initial Phase I solid tumor data on Celgene's lead IMiD™, Revimid™," Press Release, Jun. 2001.
Celgene Corporation, Form 424B4 (2000).
Celgene News Release, "Positive interim results presented at the VIIIth international myeloma workshop on Celgene Corporation's lead IMiD™ (REV/MID™)," May 8, 2001.
Cheson, "New drug development in non-Hodgkin lymphomas," Curr. Oncol. Rep. 3:250-259 (2001).
Choi et al., "Role of gallic acid in inflammatory allergic process," Korean Journal Physiology & Pharmacology, 10(2):101-108 (2006) (abstract only).
Chu et al., "Principles of cancer management: Chemotherapy," in Cancer: Principles and Practice of Oncology, 6th edition, De Vita et al., (eds.), Lippincott Williams & Wilkins, Philadelphia, PA Chapter 17 (2001).
Cimons, "How a body responds to drugs depends on the genes," Los Angeles Times, Jul. 24, 2000.
Collins et al., "Potential roles for preclinical pharmacology in phase 1 clinical trials," Cancer Treat. Rep., 70:73-80 (1986).
Corral et al., "Differential cytokine modulation and T cell activation by two distinct classes of thalidomide analogues that are potent inhibitors of TNF-α," J. Immunol. 163:380-386 (1999).
Corral et al., "Immunomodulation by thalidomide and thalidomide analogues," Ann. Rheum. Dis., 58(Suppl 1):I107-I113 (1999).
Crane et al., "Immunomodulatory drugs," Cancer Investigation 23:625-634 (2005).
D'Amato et al., "Mechanism of action of thalidomide and 3-aminothalidomide in multiple myeloma," Semin. Oncol., 28:597-601 (2001).
D'Amato et al., "Thalidomide is an Inhibitor of Angiogenesis," Proc. Natl. Acad. Sci. USA, 91(9):4082-4085 (1994).
Damaj et al., "Thalidomide therapy induces response in relapsed mantle cell lymphoma," Leukemia 17:1914-1915 (2003).
Dancey et al., "Neutrophil kinetics in man," J. Clin. Invest. 58:705-715 (1976).
Davies et al., "Thalidomide and immunomodulatory derivatives augment natural killer cell cytotoxicity in multiple myeloma," Blood, 98(1):210-216 (2001).
Devita et al., eds., "Plasma cell neoplasm." In Cancer Principles & Practice of Oncology, 5th Ed.; Lippincott-Raven Publishers, pp. 2344-2379 (1997).
Dimopoulos et al., "Thalidomide and dexamethasone combination for multiple myeloma refractory to dexamethasone-based reginens," Blood 96(Supp):286b (2000).
Dimopoulos et al., "Thalidomide and dexamethasone combination for refractory multiple myeloma," Ann. Oncol. 12:991-995 (2001).
Dishman et al., "Pharmacists'ranscript role in clozapine therapy at a veterans affairs medical center," Am. J. Hosp. Pharm. 51:899-901 (1994).
Drach et al., "Treatment of mantle cell lymphoma: Targeting the microenvironment," Expert Rev. Anticancer Ther. 5:477-485 (2005).
Dredge et al., "Immunological effects of thalidomide and its chemcial and functional analogs," Crit. Rev. Immunol., 22(5&6):425-437 (2002).
Dredge et al., "Novel thalidomide analogues display anti-angiogenic activity independently of immunomodulatory effects," Br. J. Cancer, 87(10):1166-1172 (2002).
Dredge et al., "Protective antitumor immunity induced by a costimulatory thalidomide analog in conjunction with whole tumor cell vaccination is mediated by increased Th1-type immunity," J. Immunol. 168:4914-4919 (2002).
Dredge et al., "Thalidomide analogs as emerging anti-cancer drugs," Anti-Cancer Drugs, 14:331-335 (2003).

Durie and Stepan, "Efficacy of low dose thalidomide in multiple myeloma," Eur. J. Oncol. 1:1-8 (2000).
Dykes, "Genes, disease and medicine," Br. J. Clin. Pharmacol., 42:683-695 (1996).
Edwards, "Thalidomide: Is there a silver lining?" Science News 131:198 (1987).
Elliot et al., "The proteasome: A new target for novel drug therapies," Am. J. Clin. Pathol. 116:637-646 (2001).
EORTC Pharmacokinetics and Metabolism Group, "Pharmacokinetically guided dose escalation in phase I clinical trials. Commentary and proposed guidelines," Eur. J. Cancer Clin. Oncol., 23(7):1083-1087 (1987).
FDA Guideline for Industry, "International conference on harmonisation; dose-response information to support drug regisration; guideline; availability," 59 FR 55972-01, 1994 WL 615579 (1994).
Figg et al., "Pharmacokinetics of thalidomide in an elderly prostate cancer population," J. Pharm. Sci. 88:121-125 (1999).
Filella et al., "Cytokines (IL-6, TNF-alpha, IL-1 alpha) and soluble interleukin-2 receptor as serum tumor markers in multiple myeloma," Cancer Detect. Prev. 20:52-56 (1996).
Foerster et al., "Effects of thalidomide and EM12 on the synthesis of TNF-α in coclutures of human monocytes and lymphocytes," Abstract 517 (1995).
Friedman et al., "Introduction to clinical trials" Fundamentals of Clinical Trials, $3^{rd}$ edition, Springer, New York, NY, Chapter 1 (1998).
Fujita et al., "Thalidomide and its analogues inhibit lipoplysaccharide-mediated induction of cyclooxygenase-2," Clin. Cancer Res., 7:3349-3355 (2001).
Fuse et al., "Prediction of the maximal tolerated dose (MTD) and therapeuttic effect of anticancer drugs inhumans: integration of pharmacolinetics with pharmacodynamics and toxicodynamics," Cancer Treat. Rev., 21:133-157 (1995).
Gahrton et al., "Progress in haematopoietic stem cell transplantation for multiple myeloma," J. Intern. Med. 248:185-201 (2000).
Gardner et al., "Assessing the effectiveness of a computerized pharmacy system." In Decision Support Systems in Critical Care; Shabot et al., eds.; pp. 174-183 (1994).
Glasmacher et al., "Oral idarubicin, dexamethasone and vincristine (VID) in the treatment of multiple myeloma," Leukemia 11:S22-S26 (1997).
Grönroos et al., "A medication database—a tool for detecting drug interactions in hospital," Eur. J. Clin. Pharmacol. 53:13-17 (1997).
Gupta et al., "Adherence of multiple myeloma cells to bone marrow stromal cells upregulates vascular endothelial growth factor secretion: therapeutic applications," Leukemia, 15(12):1950-1961 (2001).
Hamera et al., "Alcohol, cannabis, nicotine, and caffeine use and symptom distress in Schizophrenia," J. Nerv. Ment. Dis. 183:559-565 (1995).
He et al., "Synthesis of thalidomide analogs and their biological potential for treatment of graft versus host disease," 206th ACS National Meeting 0-8412-2620-2, American Chemical Society, Chicago, IL, Abstract 216 (1993).
Heger et al., "Embryotoxic effects of thalidomide derivatives in the non-human primate callithrixjacchus. IV teratogenicity of µg/kg doses of the EMJ 2 enantiomers," Teratog. Carcinog. Mutagen. 14:115-122 (1994).
Hideshima et al., "Novel therapies targeting the myeloma cell and its bone marrow microenvironment," Semin. Oncol. 28:607-612 (2001).
Hideshima et al., "The proteasome inhibitor PS-341 inhibits growth, induces apoptosis, and overcomes drug resistance in human multiple myeloma cells," Cancer Res. 61:3071-3076 (2001).
Hideshima et al., "Thalidomide (Thal) and its analogs overcome drug resistance of human multiple myeloma (MM) cells to conventional therapy," Abstract 1313, American Society of Hematology, Dec. 1-5, 2000.
Hideshima et al., "Thalidomide and its analogs overcome drug resistance of human multiple myeloma cells to conventional therapy," Blood 96(9):2943-2950 (2000).
Hochster et al., "Activity and pharmacodynamics of 21-Day topotecan infusion in patients with ovarian cancer previously treated with

(56) References Cited

OTHER PUBLICATIONS platinum-based chemotherapy. New York Gynecologic Oncology Group," *J. Clin. Oncol.* 17:2553-2561 (1999).
Hus et al., "Thalidomide treatment of resistant or relapsed multiple myeloma patients," *Haematologica* 86:404-408 (2001).
Jagannath et al., "Pomalidomide (POM) with or without low-dose dexamethasone (LoDEX) in patients (Pts) with relapsed and refractory multiple myeloma (RRMM): MM-002 phase II age subgroup analysis," *J. Clin. Oncol.* 31, Abstrct 1# 8532, (2013).
Jönsson, "Chemical structure and teratogenic properties. 3. A review of available data on structure-activity relationships and mechanism of action of thalidomide analogues," *Acta Pharm. Suec.* 9:521-542 (1972).
Jourdan et al., "Tumor necrosis factor is a survival and proliferation factor for human myeloma cells," *Eur. Cytokine Netw.* 10:65-70 (1999).
Keravich et al., "Challenges of thalidomide distribution in a hospital setting," *Am. J. Health Syst. Pharm.* 56:1721-1725 (1999).
Kibbe ed., Handbook of Pharmaceutical Excipients, 3rd edition, pp. 160-162 (2000).
Klausner et al., "Thalidomide as an anti-TNF-alpha inhibitor: implications for clinical use," *Clin. Immunol. Immunopathol.*, 81(3):219-223 (1996).
Klausner et al., "The effect of thalidomide on the pathogenesis of human immunodeficiency virus type 1 and M. tuberculosis infection," *J. Acquir. Immune Defic. Syndr. Hum. Retroviol.*, 11(3):247-257 (1996).
Knight, "Cancer patients ahead of FDA on thalidomide use," *Washington Post* Jun. 25, 2001.
Kosten et al., "Substance abuse and Schizophrenia: Editors' Introduction," *Schizophrenia Bulletin* 23:181-186 (1997).
Kropff et al., "Hyperfractionated cyclophosphamide in combination with pulsed dexamethasone and thalidomide (hyper-CDT) in primary refractory or relapsed multiple myeloma," *Blood*, 96(11):168a (2000).
Kumar et al., "Thalidomide and lenalidomide in the treatment of multiple myeloma," *Eur. J. Cancer*, 42:1612-1622 (2006).
Kyle et al., "Therapeutic application of thalidomide in multiple myeloma," *Semin. Oncol.* 28:583-587 (2001).
Lacy et al., "Pomalidomide (CC4047) plus low-dose dexamethasone as therapy for relapsed multiple myeloma," *J. Clin. Oncol.* 27:5008-5014 (2009).
Lacy et al., "Pomalidomide plus low-dose dexamethasone in myeloma refractory to both bortezomib and lenalidomide: Comparison of 2 dosing strategies in dual-refractory disease," *Blood* 118:2970-2975 (2011).
Langbein, "Celgene releases first data on Actimid in cancer patients," *Reuters News*, Jul. 8, 2002.
Lee et al., "A pilot trial of hyperfractionated thoracic radiation therapy with concurrent cisplatin and oral etoposide for locally advanced inoperable non-small-cell lung cancer: a 5-year follow-up report," *Int. J. Radiat. Oncol. Biol. Phys.* 42:479-486 (1998).
Lentzsch et al., "3-amino-phtalimido-glutarimide (S-3APG) inhibits angiogenesis and growth in drug resistant multiple myeloma (MM) in vivo," Abstract 1976, American Society of Hematology, 43rd Annual Meeting Orlando, Florida, Dec. 7-11, 2001.
Lentzsch et al., "Immunomodulatory analogs of thalidomide inhibit growth of Hs sultan cells and angiogenesis in vivo," *Leukemia*, 17:41-44 (2003).
Lentzsch et al., "Immunomodulatory derivatives (IMiDs) of thalidomide (Thal) inhibit the proliferation of multiple myeloma (MM) cell lines and block VEGF-induced activation of the MAPK-pathway," *Blood* 96:579 (Abstract# 2486) (2000).
Lentzsch et al., "S-3-amino-phthalimido-glutarimide inhibits angiogenesis and growth of B-cell neoplasias in mice", *Cancer Research* 62:2300-2305 (2002).
Linder et al., "Pharmacogenetics: a laboratory tool for optimizing therapeutic efficiency," *Clin. Chem.*, 43(2):254-266 (1997).
Linnarsson, "Decision support for drug prescription integrated with computer-based patient records in primary care," *Med. Inform.* 18:131-142 (1993).
Lipkin, "Deriving new drugs from thalidomide," *Science News* 148:171 (1995).
Mann et al., "Passage of chemicals into human and animal semen: mechanisms and significance," *Crit. Rev. Toxicol.* 11:1-14 (1982).
Marriott et al., "Immunotherapeutic and antitumour potential of thalidomide analogues," *Expert Opin. Biol. Ther.* 1:1-8 (2001).
Marriott et al., "Immunotherapeutic and antitumour potential of thalidomide analogues," *Expert Opin. Biol. Ther.*, 1(4):675-682 (2001).
Marriott et al., "Thalidomide and its analogues have distinct and opposing effects on TNF-alpha and TNFR2 during co-stimulation of both CD4+ and CD8+ T cells," *Clin. Exp. Immunol.*, 130:75-84 (2002).
Marwick, "Thalidomide back—under strict control," *JAMA* 278:1135-1137 (1997).
Menill, "Substance Abuse and Women on Welfare," in *National Center on Addiction and Substance Abuse at Columbia University*, Jun. 1994.
Milner et al., "Attitudes of young adults to prenatal screening and genetic correction for human attributes and psychiatric conditions," *Am. J. Med. Genet.*, 76:111-119 (1998).
Mitchell et al., "A pregnancy-prevention program in women of childbearing age receiving isotretinoin," *N. Engl. J. Med.* 333:101-106 (1995).
Mitsiades et al., "Concepts in the use of TRAIL/Apo2L: An emerging biotherapy for myeloma and other neoplasias," *Expert Opin. Investig. Drugs* 10:1521-1530 (2001).
Mitsiades et al., "Apoptic signaling induced by immunomodulatory thalidomide analogs in human multiple myeloma cells: therapeutic implications," *Blood*, 2002, 99:4525-4530, American Society of Hematology.
Montero et al., "Economic study of neutropenia induced by myelotoxic chemotherapy," *Pharm. World Sci.* 16:187-192 (1994).
Moreira et al., "Thalidomide exerts its inhibitory action on tumor necrosis factor a by enhancing mRNA degradation," *J. Exp. Med.*, 177(6):1675-1680 (1993).
Morgan et al., "Lenalidomide (Revlimid), in combination with cyclophosphamide and dexamethasone (RCD), is an effective and tolerated regimen for myeloma patients," *Br. J. Haematol.* 137:268-269 (2007).
Muller et al., "Amino-substituted thalidomide analogs: potent inhibitors of TNF-alpha production.," *Bioorg. Med. Chem. Lett.*, 9(11):1625-1630 (1999).
Muller, Thalidomide: From tragedy to new drug discovery, *Chemtech* 27:21-25 (1997).
Mundt, "Interactive voice response systems in clinical research and treatment," *Psychiatr. Serv.* 48:611-612, 623 (1997).
National Cancer Institute, Common Toxicity Criteria Manual, Ver. 2.0, Jun. 1, 1999.
NCT00480363: "QUIREDEX: Revlimid (lenalidomide) and dexamethasone (ReDex) treatment versus observation in patients with smoldering multiple myeloma with high risk of progression (QUIREDEX)," (2013).
Noguelra et al., "Effect of thalidomide and some derivatives on the adhesion of lymphocytes to endothelial cells," Abstract 518 (1995).
Olson et al., "Thalidomide (N-phthaloylglutamimide) in the treatment of advanced cancer," *Clin. Pharm. Ther.*, 6(3):292-297 (1965).
Palumbo et al., "Low-dose thalidomide plus dexamethasone is an effective salvage therapy for advanced myeloma," *Haematologica* 86:399-403 (2001).
Pastuszak et al., "Use of the retinoid pregnancy prevention program in Canada: Patterns of contraceptive use in women treated with isotretinoin and etretinate," *Reprod. Toxicol.* 8:63-68 (1994).
Pestotnik et al., "Therapeutic antibiotic monitoring: Surveillance using a computerized expert system," *Am. J. Med.* 88:43-48 (1990).
Peterson et al., "Expanding the scope of crystal form evaluation in pharmaceutical science," *J. Pharm. Pharmaceut. Sci.*, 9(3):317-326 (2006).
Piper et al., "Anti-inflammatory immunosuppressive thalidomide analogs. Screening," *Int. J. Leprosy* 49:511-512 (1981).

(56) References Cited

OTHER PUBLICATIONS

Powell et al., "Guideline for the clinical use and dispensing of thalidomide," *Postgrad. Med. J.* 70:901-904 (1994).
Pro et al., "Phase II study of thalidomide in patients with recurrent Hodgkin's disease (HD) and non-Hodgkin's lymphoma (NHL)," *Blood* 98:246b (Abstract# 4712) (2001).
Querfeld et al., "Preliminary results of a phase II study of CC-5013 (lenalidomide, revlimid®) in patients with cutaneous T-cell lymphoma," *Blood* 106:936a-937a (2005).
Raje et al., "Thalidomide and immunomodulatory drugs as cancer therapy," *Curr. Opin. Oncol.*, 14:635-640 (2002).
Raje et al., "Thalidomide—a revival story," *N. Engl. J. Med.* 341(21):1606-1609 (1999).
Rajkumar et al., "Lenalidomide plus high-dose dexamethasone versus lenalidomide plus low-dose dexamethasone as initial therapy for newly diagnosed multiple myeloma: an open-label randomised controlled trial," *Lancet* 11:29-37 (2010).
Rajkumar et al., "Phase III trial of lenalidomide plus highdose dexamethasone versus lenalidomide plus low-dose dexamethasone in newly diagnosed multiple myeloma (E4A03): A trial coordinated by the Eastern Cooperative Oncology Group," *J. Clin. Oncol.* 25:18S (2007).
Rajkumar et al., "Thalidomide plus dexamethasone (Thal/Dex) and thalidomide alone (Thal) as first line therapy for newly diagnosed myeloma (MM)," *Blood* 96(Supp.):168a (2000).
Rajkumar et al., "Combination therapy with lenalidomide plus dexamethasone (Rev/Dex) for newly diagnosed myeloma," *Blood*, 106(13):4050-4053 (2005).
Rajkumar et al., "Thalidomide in the treatment of plasma cell malignancies," *J. Clin. Oncol.* 19:3593-3595 (2001).
Rajkumar, "Thalidomide in multiplem myeloma," *Oncology* 14:11-16 (2000).
Ratain, "Pharmacology of Cancer Chemotherapy." in *Cancer: Principles & Practice of Oncology*, pp. 335-459 (2001).
Rautio et al., "Prodrugs: design and clinical applications," *Nat. Rev. Drug Discov.*, 7:255-270 (2008).
Reiman et al., "Meeting synopsis, VIII International Myeloma Workshop, Banff Springs Hotel, Banff, Alberta, Canada, May 4-8, 2001," *Eur. J. Haematol.* 67:199-202 (2001).
Ribatti et al., "Angiogenesis spectrum in the stroma of B-cell non-Hodgkin's lymphomas. An immunohistochemical and ultrastructural study," *Eur. J. Haematol.* 56:45-53 (1996).
Richardson et al., "A randomized phase 2 study of lenalidomide therapy for patients with relapsed or relapsed and refractory multiple myeloma," *Blood* 108:3458-3464 (2006).
Richardson et al., "Thalidomide in multiple Myeloma," *Biomed. Pharmacother.* 56:115-128 (2002).
Richardson et al., "Thalidomide: Emerging role in cancer medicine," *Ann. Rev. Med.* 53:629-657 (2002).
Richardson et al., "A multi-center, randomized, phase II study to evaluate the efficacy and safety of two CDC-5013 dose regimens when used alone or in combinatin with dexamethasone (Dex) for the treatment of relapsed or refractory multiple myeloma (MM)," Abstract 386, *Blood*, 100(11 Part 1):104a (2002).
Richardson et al., "A phase 1 study of oral CC5013, an immunomodulatory thalidomide (Thal) derivative, in patients with relapsed and refractory multiple myeloma (MM)," *Blood* 98:775a (2001).
Richardson et al., "A phase 1/2 multi-center, randomized, open label dose escalation study to determine the maximum tolerated dose (MTD), safety, and efficacy of pomalidomide (POM) alone or in combination with low-dose dexamethasone (DEX) in patients (PTS) with relapsed and refractory multiple myeloma (RRMM) who have received prior treatment (TX) that includes lenalidomide (LEN) and bortezomib (BORT)," *Haematologica*, 96:S31 (2011).
Richardson et al., "A phase I study of the safety and efficacy of CC5013 treatment for patients with relapsed multiple myeloma: Preliminary results," VIII the International Myeloma Workshop, Banff, Alberta, Canada, May 4-8, 2001; Abstract #P230.

Richardson et al., "Immunomodulatory drug CC-5013 overcomes drug resistance and is well tolerated in patients with relapsed multiple myeloma," *Blood* 100:3063-3067 (2002).
Robert et al., "Phase I and pharmacologic study of 7- and 21-day continuous etoposide infusion in patients with advanced cancer," *Cancer Chemother. Pharmacol.* 38:459-465 (1996).
Rubinstein et al., "Phase I clinical trial design," Biometric Research Branch, National Cancer Institute (2003).
Samlowski et al., "Evaluation of gemcitabine in patients with recurrent or metastatic squamous cell carcinoma of the head and neck: A southwest oncology group phase II study," *Invest. New Drugs* 19:311-315 (2001).
Sampaio et al., "Prolonged treatment with recombinant interferon gamma induces erythema nodosum leprosum in lepromatous leprosy patients," *J. Exp. Med.* 175:1729-1737 (1992).
Sampaio et al., "Thalidomide selectively inhibits tumor necrosis factor alpha production by stimulated human monocytes," *J. Exp. Med.* 173:699-703 (1991).
Schey et al., "Phase I Study of an Immunomodulatory Thalidomide Analog, CC-4047, in Relapsed or Refractory Multiple Myeloma," *J. Clin. Oncol.* 22(16):3269-3276 (2004).
Schey et al., "Pomalidomide therapy for myeloma," *Expert Opin. Invest. Drugs* 20:691-700 (2011).
Schey et al., "A phase I study of an immunomodulatory thalidomide analogue (CC4047) in relapse/refractory multiple myeloma," *International Society for Experimental Hematology, Abstract #248*, (2002).
Schey, "Thalidomide in the management of multiple myeloma," *Hematology* 7:291-299 (2002).
Schlossman et al., "Bone marrow transplatation in multiple myeloma," *Curr. Opin. Oncol.* 11:102-108 (1999).
Seppa, "Thalidomide combats myeloma blood cancer," *Science News* 156:326 (1999).
Shaughnessy et al., "Global gene expression analysis shows loss of c-myc and IL-6 receptor gene mRNA after exposure of myeloma to thaldomide and IMiD," Abstract 2485, American Society of Hematology, 42$^{nd}$ Annual Meeting San Francisco, CA, Dec. 1-5, 2000.
Shinn et al., "Development of a computerized drug interaction database (MEDICOM) for use in a patient specific environment," *Drug Inf. J.* 17:205-210 (1983).
Siegel et al., "Long-term safety and efficacy of pomalidomide (POM) with or without low-dose dexamethasone (LoDEX) in relapsed and refractory multiple myeloma (RRMM) patients enrolled in the MM-002 phase II trial," *J. Clin. Oncol.* 31, 2013 (Abstract No. 8588).
Singhal et al., "Antitumor activity of thalidomide in refractory multiple myeloma," *N. Engl. J. Med.*, 341(21):1565-1571 (1999).
Smith et al., "Design and resutls of phase I cancer clinical trials: three-year experience at M.D. Anderson Cancer Center," *J. Clin. Oncol.*, 14:287-295 (1996).
Smith, R. et al., "Studies on the Relationship Between the Chemical Structure and Embryotoxic Activity of Thalidomide and Related Compounds," in *A Symposium on Embryopathic Activity of Drugs*, J. & A. Churchill Ltd., Session 6, pp. 194-209 (1965).
Sorbera et al., "CC-5013. Treatment of multiple myeloma. Treatment of Melanoma. Treatment of myelodysplastic syndrome. Angiogenesis inhibitor. TNF-α production inhibitor," *Drugs of the Future*, 28(5):425-431 (2003).
Soyka et al., "Prevalence of alcohol and drug abuse in schizophrenic inpatients," *Eur. Arch. Psychiatry Clin. Neurosci.* 242:362-372 (1993).
Srkalovic et al. "Use of melphalan, thalidomide, and dexamethasone in treatment of refractory and relapsed multiple myeloma," *Med. Oncol.* 19:219-226 (2002).
Steed, "The role of co-cystals in pharmaceutical design," *Trends in Pharmacol. Sci.*, 34(3):185-193 (2013).
Steiner et al., "The assessment of refill compliance using pharmacy records: methods, validity, and applications," *J. Clin. Epidemiol.* 50:105-116 (1997).
Stirling et al., "Thalidomide. A surprising recovery," *J. Am. Pharm. Assoc.* NS37:306-313 (1997).
Stirling, "Thalidomide: A novel template for anticancer drugs," *Seminars Oncology* 28:602-606 (2001).

(56) References Cited

OTHER PUBLICATIONS

Szelényi et al., "Cyclophosphamide, adriamycin and dexamethasone (CAD) is a highly effective therapy for patients with advanced multiple myeloma," *Ann. Oncol.* 12:105-108 (2001).
THALOMID™ (thalidomide) Capsules Revised Package Insert (Jul. 15, 1998).
The Comprehensive Guide to Banff, Understanding the VIIIth International Myeloma Workshop published by the International Myeloma Foundation (2001).
Thomas et al., "Current role of thalidomide in cancer treatment," *Curr. Opin. Oncol.* 12:564-573 (2000).
Transcript of the Forty-Seventh Meeting of the Dermatologic and Ophthalmic Drugs Advisory Committee (Sep. 4, 1997).
Transcript of the Forty-Seventh Meeting of the Dermatologic and Ophthalmic Drugs Advisory Committee (Sep. 5, 1997).
Tseng et al., "Rediscovering thalidomide: a review of its mechanism of action, side effects, and potential uses," *J. Am. Acad. Dermatol.* 35:969-979 (1996).
Tsenova et al., "Use of IMiD3, a thalidomide analog, as an adjunct to therapy for experimental tuberculous meningitis," *Antimicrob Agents Chemother.*, 46(6):1887-1895 (2002).
Vacca et al., "Angiogenesis in B cell lymphoproliferative diseases. Biological and clinical studies," *Leuk. Lymphoma* 20:27-38 (1995).
Vanchieri, "Preparing for thalidomide's comeback," *Annals Internal Med.*, 127(10):951-952 (1997).
Verma, "Gallic acid: molecular rival of cancer," *Environ. Toxicol. Pharmacol.*, 35(3):473-485 (2013).
Vij et al., "Pomalidomie (POM) with Low-Dose Dexamethasone (LoDex) in Patients with Relapsed and Refractory Multiple Myeloma (RRMM): Outcomes Based on Prior Treatment Exposure," presented at 54th ASH Annual Meeting and Exposition, Atlanta, Georgia, Dec. 8-11, 2012, Abstract #4070.
Vippagunta et al., "Crystalline solids," *Adv. Drug Deliv. Rev.*, 48(1):3-26 (2001).
Vogelsang et al., "Thalidomide for the treatment of chronic graft-versus-host disease," *N. Engl. J. Med.* 326:1055-1058 (1992).
Weber et al., "Thalidomide alone or with dexamethasone for multiple myeloma," *Blood* 94:604 (1999).
Weber et al., "Thalidomide with dexamethasone of resistant multiple myeloma," *Blood* 96:167 (2000).
Welte et al., "Influence of socially desirable responding in a study of stress and substance abuse," *Alcohol Clin. Exp. Res.* 17:758-761 (1993).
Wilson et al., "Response to thalidomide in chemotherapy-resistant mantle cell lymphoma: a case report," *Br. J. Haematol.* 119:128-130 (2002).
Wolf et al., "Science, medicine, and the future pharmacogentics," *BMJ*, 320:987-990 (2000).
Wolff ed., *Burger's Medicinal Chemistry and Drug Discovery*, 5th Edition, vol. 1, John Wiley & Sons, Inc., pp. 975-977 (1995).
Yuen et al., "Phase I study of an antisense oligonucleotide to protein kinase C-α (ISIS 3521/CGP 64128A) in patients with cancer," *Clin. Cancer Res.* 5:3357-3363 (1999).
Zangari et al., "Increased risk of deep-vein thrombosis in patients with multiple myeloma receiving thalidomide chemotherapy," *Blood* 98:1614 (2001).
Zangari et al., Results of phase I study of CC-5013 for the treatment of multiple myeloma (MM) patients who relapse after high dose chemotherapy (HDT), *Blood* 98(11), Abstract# 3226 (2001).
Zangari et al., "Thrombogenic activity of doxorubicin in myeloma patients receiving thalidomide: implications for therapy," *Blood*, 100:1168-1171 (2002).
Zeldis et al., "S.T.E.P.S.: A comprehensive program for controlling and monitoring access to thalidomide," *Clin. Ther.* 21:319-330 (1999).
Celgene Corporation, POMALYST® (pomalidomide) packaging label, Retrieved online on Dec. 14, 2017, retrieved online at <http://www.pomalyst.com/?pi=yes&gclid—CMP4keDY-tMCFZOCfgods7oPsA>, revised Jun. 2016.
Dimartino et al., "Preparation and physical characterization of forms II and III of paracetamol," *J. Thermal. Anal.*, 48(3):447-458 (1997).
Gennaro, *Remington: The Science and Practice of Pharmacy*, 20th Ed., Lipincott Williams & Wilkins, pp. 172-182 (2000).
Knapman, "Polymorphic Predictions: Understanding the nature of crystalline compounds can be critical in drug development and manufacture," *Modern Drug Discoveries*, 53-57 (2000).
*The United States Pharmacopeia*, 37th Edition, United States Pharmacopeial Convention, Inc., Rockville, MD, pp. 503-509 (2014).
Anonymous, "CMU seed fund project on detection and control of pharmaceutical polymorphism," retrieved online. Retrieved from URL: http://andrew.cmu.edu/user/suter/polymorph.html> retrieved on Apr. 3, 2008, 3 pages (2002).
Anonymous, "Crystallization," *Kirk-Othmer Encyclopedia of Chemical Technology*, John Wiley & Sons, Inc., 8th edition, pp. 95-147 (2002).
Anonymous, "X-ray diffraction," *U.S. Pharmacopia #23, National Formulary #18*, pp. 1843-1844 (1995).
Anonymous, *Concise Encyclopedia Chemistry*, Walter de Gruyter, New York pp. 872-873 (1993).
Bernstein, *Polymorphism in Molecular Crystals*, Clarendon Press, Oxford, pp. 115-118 and 272 (2002).
Braga et al., "Making crystals from crystals: a green route to crystal engineering and polymorphism," *J. Royal Soc. Chem.*, pp. 3635-3645 (2005).
Davidovich et al., "Detection of polymorphism by powder x-ray diffraction: interference by preferred orientation," *Am. Pharm. Rev.*, 7(1):10, 12, 14, 16 and 100 (2004).
Dean, *Analytical Chemistry Handbook*, McGraw-Hill, Inc., New York, pp. 10.24-10.26 (1995).
Doelker, "Crystallline modifications and polymorphous changes during drug manufacture," *Ann. Pharm. Fr.*, 60:161-176 (2002) English translation attachtaded.
Doelker, "Physiocochemical behavior of active substances their consequences for the feasibility and stability of pharmaceutical forms," *S.T.P. Pharma Pratiques*, 9(5):399-409 (1999) English translation attached.
Guillory, "Generation of polymorphs, hydrates, solvates, and amorphous solids," *Polymorphism in Pharmaceutical Solids*, Marcel Dekker, Inc., New York, pp. 183-226 (1999).
Ivanisevic eta l., "Uses of x-ray powder diffraction in the pharmaceutical industry," *Pharmaceutical Sciences Encyclopedia: Drug Discovery, Development, and Manufacturing*, Gad S., Ed., John Wiley & Sons, Inc., pp. 1-42 (2010).
Jain et al., "Polymorphism in pharmacy," *Indian Drugs*, 23(6):315-329 (1986).
Muzaffar et al., "Polymorphism and drug availability," *J. Pharmacy*, 1(1):59-66 (1979).
Nie et al., "Source analysis and synthesis of pomalidomide impurities," *CAPLUS*, Accession No. 1743748 (2015).
Otsuka et al., Effect of polymorphic forms of bulk powders on pharmaceutical properties of carbamazepine granules, *Chem. Pharm. Bull.*, 47(6):852-856 (1999).
Rodriguez-Spong et al., "General principles of pharmaceutical solid polymorphism: a supramolecular perspective," *Adv. Drug Del. Rev.*, 56:241-274 (2004).
Seddon, "Pseudopolymorph: a polemic," *Am. Chem. Soc.*, 4(6):1087 (2004).
Singhal et al., "Drug polymorphism and dosage form design: a practical prspective," *Adv. Drug Del. Rev.*, 46:335-347 (2004).
Taday et al., "Using terahertz pulse spectroscopy to study the crystalline structure of a drug: a case study of the polymorphs of ranitidine hydrochloride," *J. Pharm. Sci.*, 92(4):831-838 (2003).

\* cited by examiner

CRYSTALLINE 4-AMINO-2-(2,6-DIOXOPIPERIDINE-3-YL)ISOINDOLINE-1,3-DIONE DIHYDRATE, COMPOSITIONS AND METHODS OF USE THEREOF

This application is a continuation application of U.S. patent application Ser. No. 15/849,285, filed Dec. 20, 2017, which claims priority to U.S. Provisional Patent Application No. 62/511,878, filed May 26, 2017, the entirety of each of which are incorporated herein by reference.

FIELD

Provided herein is a crystalline 4-amino-2-(2,6-dioxopiperidine-3-yl)isoindoline-1,3-dione dihydrate. Pharmaceutical compositions comprising such solid and methods of use for treating, preventing, and managing various disorders are also provided herein.

BACKGROUND

Many compounds can exist in different crystal forms, or polymorphs, which exhibit different physical, chemical, and spectroscopic properties. For example, certain polymorphs of a compound may be more readily soluble in particular solvents, may flow more readily, or may compress more easily than others. See, e.g., P. DiMartino, et al., *J. Thermal Anal.*, 48:447-458 (1997). In the case of drugs, certain solid forms may be more bioavailable than others, while others may be more stable under certain manufacturing, storage, and biological conditions.

Polymorphic forms of a compound are known in the pharmaceutical arts to affect, for example, the solubility, stability, flowability, fractability, and compressibility of the compound, as well as the safety and efficacy of drug products comprising it. See, e.g., Knapman, K. *Modern Drug Discoveries*, 2000, 53. Therefore, the discovery of new polymorphs of a drug can provide a variety of advantages.

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Pomalidomide has a chemical name of 4-amino-2-(2,6-dioxopiperidine-3-yl)isoindoline-1,3-dione. Pomalidomide is a compound that inhibits, for example, LPS induced monocyte TNFα, IL-1β, IL-12, IL-6, MIP-1, MCP-1, GM-CSF, G-CSF, and COX-2 production, and may be used in treating various disorders. See, e.g., U.S. Pat. Nos. 5,635,517, 6,316,471, 6,476,052, 7,393,863, 7,629,360, 7,863,297, 8,198,262, 8,673,939, 8,735,428, 8,759,375, 8,722,647, and 9,282,215. Pomalidomide has direct anti-myeloma tumoricidal and immunomodulatory activities, and inhibits stromal cell support for multiple myeloma tumor cell growth. Pomalidomide inhibits proliferation and induces apoptosis of hematopoietic tumor cells. Additionally, pomalidomide inhibits the proliferation of lenalidomide-resistant multiple myeloma cell lines and synergizes with dexamethasone in both lenalidomide-sensitive and lenalidomide-resistant cell lines to induce tumor cell apoptosis. Pomalidomide enhances T cell- and natural killer (NK) cell-mediated immunity, and inhibits production of pro-inflammatory cytokines (e.g., TNF-α and IL-6) by monocytes. Pomalidomide also inhibits angiogenesis by blocking the migration and adhesion of endothelial cells. A molecular target of pomalidomide is cereblon, a protein that forms a ubiquitin E3 ligase complex with DNA damage-binding protein (DDBA), culin 4 (CUL4) and protein Roc 1. Pomalidomide binding to cereblon induces the polyubiquitination of two substrate proteins Ikaros (IKF1) and Aiolos (IKZF3). Pomalidomide is known to have CNS penetration. Due to its diversified pharmacological properties, pomalidomide is useful in treating, preventing, and/or managing various diseases or disorders.

Pomalidomide and methods of synthesizing pomalidomide are described, e.g., in U.S. Pat. Nos. 5,635,517, 6,335,349, 6,316,471, 6,476,052, 7,041,680, 7,709,502, and 7,994,327. The chemical structure of pomalidomide has been known since at least the 1960s, but little is known regarding solid forms. An amorphous solid and one crystalline form (anhydrous) have been described in WO 2013/126326. A novel crystalline form of pomalidomide is described herein.

Pomalidomide is the active ingredient in POMALYST®, which in combination with dexamethasone was approved by the FDA in 2013 for the treatment of patients with multiple myeloma who have received at least two prior therapies including lenalidomide and a proteasome inhibitor and have demonstrated a disease progression on or within 60 days of completion of the last therapy. The label for POMALYST® can be found at http://www.pomalyst.com/?pi=yes&gclid=CMP4keDY-tMCFZOCfgods7oPsA.

New polymorphic forms of 4-amino-2-(2,6-dioxopiperidine-3-yl)isoindoline-1,3-dione can further the development of formulations for the treatment of chronic illnesses, and may yield numerous formulation, manufacturing and therapeutic benefits.

SUMMARY

Provided herein is a crystalline form of pomalidomide. Also provided herein are pharmaceutical compositions comprising a crystalline form of pomalidomide. Further provided herein are methods of treating or preventing a variety of disease and disorders, which comprise administering to a patient a therapeutically effective amount of a crystalline form of pomalidomide. Also provided herein are methods of treating multiple myeloma, optionally in combination with dexamethasone.

Also provided herein are methods of preparing, isolating, and characterizing crystalline 4-amino-2-(2,6-dioxopiperidine-3-yl)isoindoline-1,3-dione dihydrate provided herein.

DEFINITIONS

Figure 1:
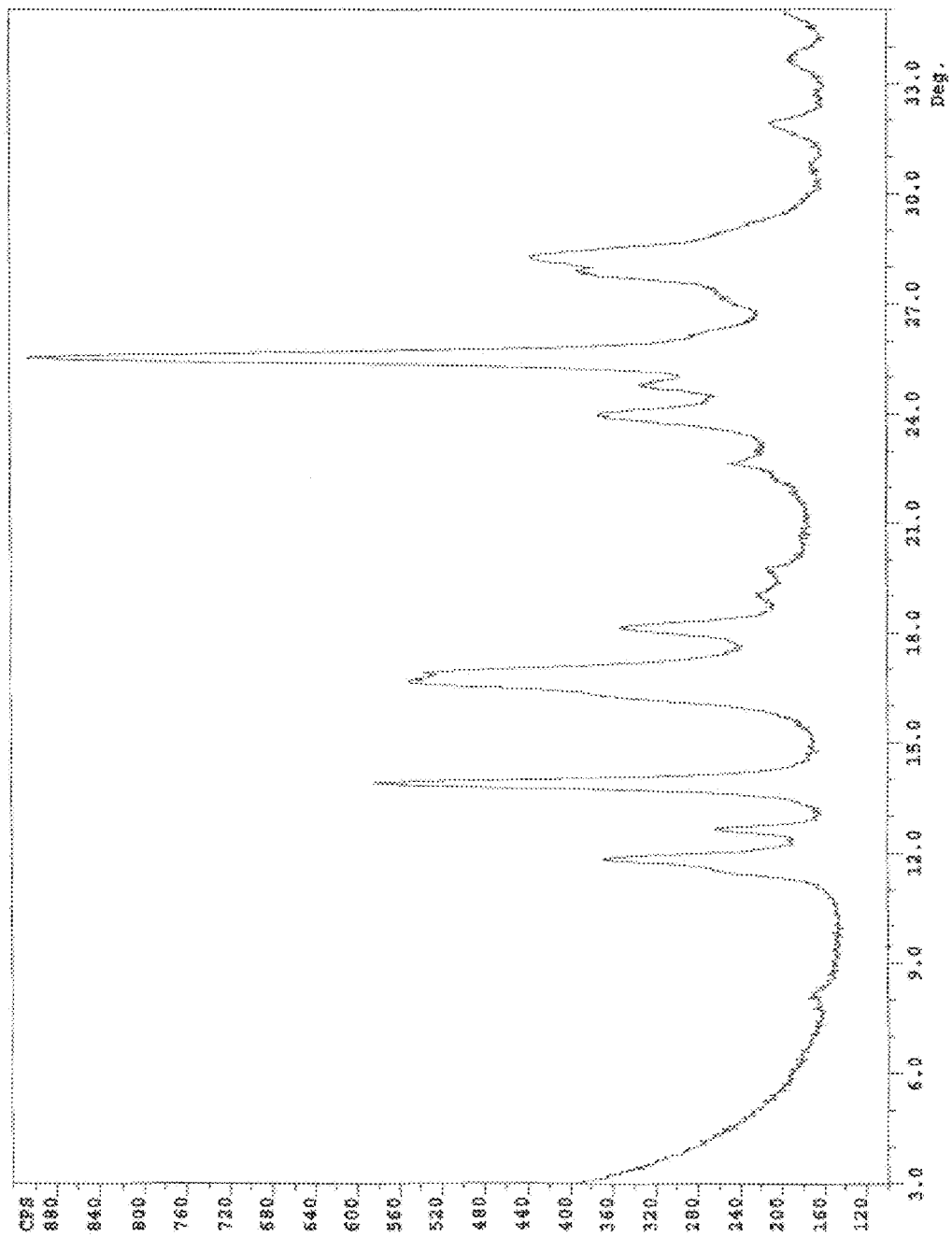
FIG. 1 provides a representative X-ray powder diffraction (XRPD) pattern of crystalline 4-amino-2-(2,6-dioxopiperidine-3-yl)isoindoline-1,3-dione dihydrate.

As used herein, and unless otherwise specified, the compound referred to herein by the name pomalidomide or 4-amino-2-(2,6-dioxopiperidine-3-yl)isoindoline-1,3-dione, corresponds to a compound of Formula (I), depicted below.

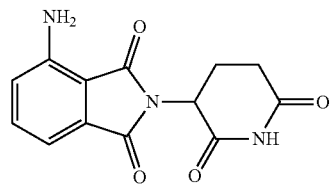

(I)

Pomalidomide can be obtained via standard, synthetic methods (see e.g., U.S. Pat. No. 5,635,517).

Unless otherwise specified, the term "crystalline" and related terms used herein, when used to describe a substance, component, product, or form, mean that the substance, component, product, or form is substantially crystalline, for example, as determined by X-ray diffraction. (see, e.g., Remington's Pharmaceutical Sciences, 20$^{th}$ ed., Lippincott Williams & Wilkins, Philadelphia Pa., 173 (2000); The United States Pharmacopeia, 37$^{th}$ ed., 503-509 (2014)).

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or XRPD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. In the context of molar ratios, "about" and "approximately" indicate that the numeric value or range of values may vary within 20%, 15%, 10%, 9%, 8%, 7%, 6%, 5%, 4%, 3%, 2%, 1.5%, 1%, 0.5%, or 0.25% of the recited value or range of values. It should be understood that the numerical values of the peaks of an X-ray powder diffraction pattern may vary from one machine to another, or from one sample to another, and so the values quoted are not to be construed as absolute, but with an allowable variability, such as ±0.2 degrees two theta (°2θ), or more. For example, in some embodiments, the value of an XRPD peak position may vary by up to ±0.2 degrees 2θ while still describing the particular XRPD peak.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the terms "solvate" and "solvated," as used herein, refer to a solid form of a substance which contains solvent. The terms "hydrate" and "hydrated"

refer to a solvate wherein the solvent is water. The term "dihydrate" refers to a hydrate containing approximately two moles of water per mole of compound.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of a particular disease.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). By "pharmaceutically acceptable," it is meant a diluent, excipient, or carrier in a formulation must be compatible with the other ingredient(s) of the formulation and not deleterious to the recipient thereof.

Unless otherwise specified, the term "subject" is defined herein to include animals, such as mammals, including, but not limited to, primates (e.g., humans), cows, sheep, goats, horses, dogs, cats, rabbits, rats, mice, and the like. In specific embodiments, the subject is a human.

Unless otherwise specified, to the extent that there is a discrepancy between a depicted chemical structure of a compound provided herein and a chemical name of a compound provided herein, the chemical structure shall control.

DETAILED DESCRIPTION

Crystalline 4-amino-2-(2,6-dioxopiperidine-3-yl)isoindoline-1,3-dione dihydrate can be prepared by the methods described herein, including the methods described in the Example below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding, solvent-drop grinding or liquid assisted grinding), microwave-induced precipitation, sonication-induced precipitation, laser-induced precipitation and precipitation from a supercritical fluid. The particle size of the resulting solid forms, which can vary, e.g., from nanometer dimensions to millimeter dimensions, can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, crystalline 4-amino-2-(2,6-dioxopiperidine-3-yl)isoindoline-1,3-dione dihydrate is characterized by physical properties, e.g., stability, solubility and dissolution rate, appropriate for pharmaceutical and therapeutic dosage forms. Moreover, while not wishing to be bound by any particular theory, crystalline 4-amino-2-(2,6-dioxopiperidine-3-yl)isoindoline-1,3-dione dihydrate is characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Certain embodiments herein provide compositions comprising crystalline 4-amino-2-(2,6-dioxopiperidine-3-yl)isoindoline-1,3-dione dihydrate. Certain embodiments provide compositions of crystalline 4-amino-2-(2,6-dioxopiperidine-3-yl)isoindoline-1,3-dione dihydrate in combination with other active ingredients. Certain embodiments provide methods of using these compositions in the treatment, prevention or management of diseases and disorders including, but not limited to, the diseases and disorders provided herein.

Certain embodiments herein provide crystalline 4-amino-2-(2,6-dioxopiperidine-3-yl)isoindoline-1,3-dione dihydrate. In one embodiment provided herein, crystalline 4-amino-2-(2,6-dioxopiperidine-3-yl)isoindoline-1,3-dione dihydrate can be obtained from a 4:1 1,4-dioxane/water mixture. In one embodiment provided herein, crystalline 4-amino-2-(2,6-dioxopiperidine-3-yl)isoindoline-1,3-dione dihydrate can be obtained from a 4:1 THF/water mixture. In one embodiment provided herein, crystalline 4-amino-2-(2,6-dioxopiperidine-3-yl)isoindoline-1,3-dione dihydrate can be obtained from an 1:1:1 acetone/water/isopropyl alcohol mixture.

In one embodiment, provided is a crystalline 4-amino-2-(2,6-dioxopiperidine-3-yl)isoindoline-1,3-dione dihydrate.

In certain embodiments, crystalline 4-amino-2-(2,6-dioxopiperidine-3-yl)isoindoline-1,3-dione dihydrate may be characterized by X-ray powder diffraction analysis.

In one embodiment, provided is a crystalline 4-amino-2-(2,6-dioxopiperidine-3-yl)isoindoline-1,3-dione dihydrate having an X-ray powder diffraction pattern comprising peaks at 13.9, 16.6, and 25.5 degrees 2θ±0.2 degrees 2θ.

In one embodiment, provided is a crystalline 4-amino-2-(2,6-dioxopiperidine-3-yl)isoindoline-1,3-dione dihydrate wherein the X-ray powder diffraction pattern further comprises peaks at 11.9, 16.9, and 28.2 degrees 2θ±0.2 degrees 2θ.

In certain embodiments, crystalline 4-amino-2-(2,6-dioxopiperidine-3-yl)isoindoline-1,3-dione dihydrate is characterized by XRPD peaks located at one, two, three, four, five, six, seven, eight, nine, ten, eleven or twelve of the following approximate positions: 11.9, 12.7, 13.9, 16.6, 16.9, 18.1, 22.6, 23.9, 24.8, 25.5, 27.8, 28.2, and 31.8 degrees 2θ. In certain embodiments, crystalline 4-amino-2-(2,6-dioxopiperidine-3-yl)isoindoline-1,3-dione dihydrate is characterized by an XRPD pattern which matches the pattern exhibited in FIG. 1. In certain embodiments, crystalline 4-amino-2-(2,6-dioxopiperidine-3-yl)isoindoline-1,3-dione dihydrate is characterized by an XRPD pattern which matches the pattern exhibited in FIG. 2. In certain embodiments, crystalline 4-amino-2-(2,6-dioxopiperidine-3-yl)isoindoline-1,3-dione dihydrate is characterized by an XRPD pattern having 1, 2, 3, 4, 5, 6, 7, 8, 9, 10, 11, 12, 13, 14, 15, 16, 17, 18, 19, 20, 21, 22, 23, 24 or 25 peaks matching peaks in a representative XRPD pattern provided herein.

In one embodiment, provided is a crystalline 4-amino-2-(2,6-dioxopiperidine-3-yl)isoindoline-1,3-dione dihydrate having an X-ray powder diffraction pattern corresponding to the representative X-ray powder diffraction pattern depicted in FIG. 1.

Figure 2:
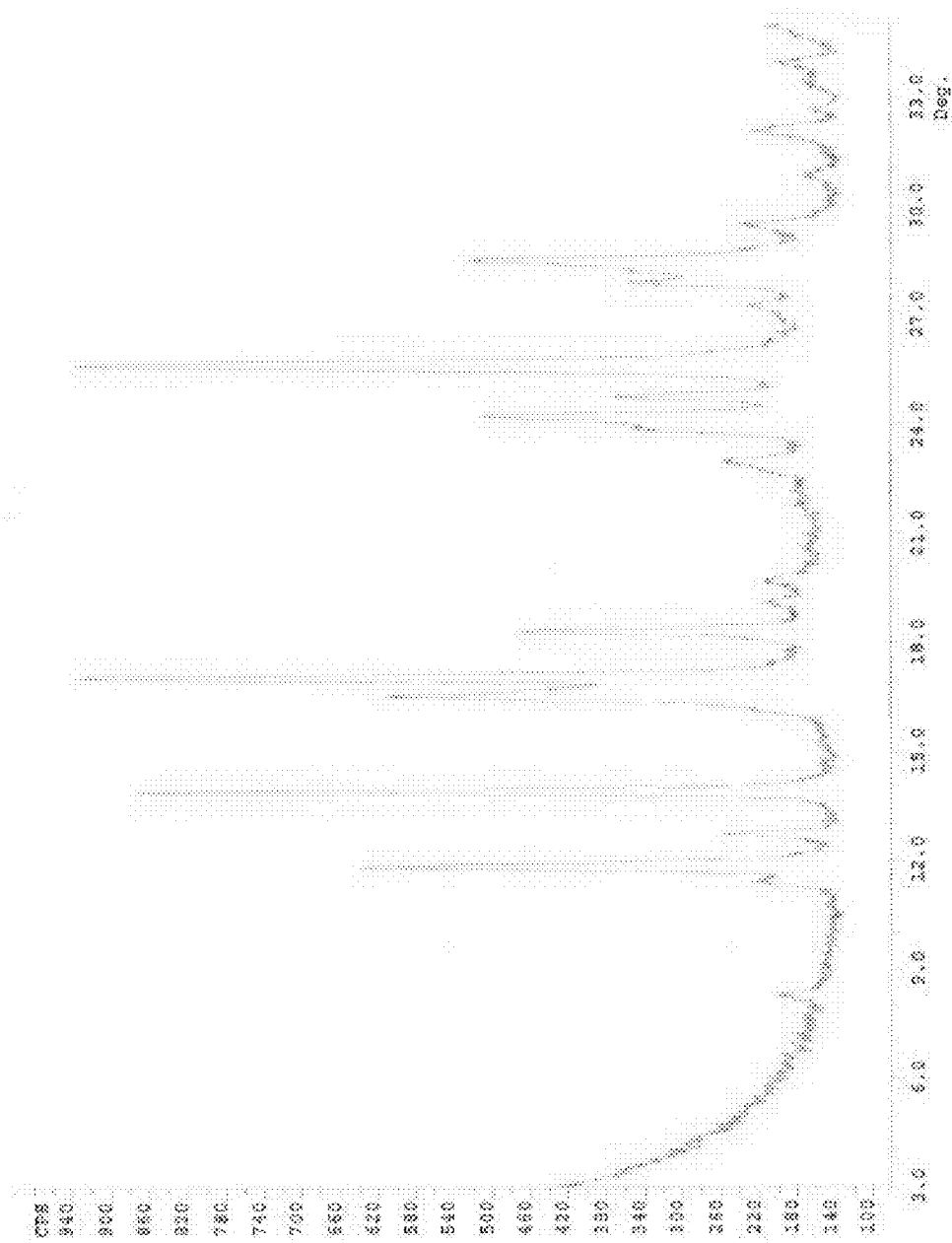
FIG. 2 provides a representative X-ray powder diffraction (XRPD) pattern of crystalline 4-amino-2-(2,6-dioxopiperidine-3-yl)isoindoline-1,3-dione dihydrate.

In one embodiment, provided is a crystalline 4-amino-2-(2,6-dioxopiperidine-3-yl)isoindoline-1,3-dione dihydrate having an X-ray powder diffraction pattern corresponding to the representative X-ray powder diffraction pattern depicted in FIG. 2.

In certain embodiments, crystalline 4-amino-2-(2,6-dioxopiperidine-3-yl)isoindoline-1,3-dione dihydrate may be characterized by thermal analysis.

In one embodiment, provided is a crystalline 4-amino-2-(2,6-dioxopiperidine-3-yl)isoindoline-1,3-dione dihydrate having a differential scanning calorimetry thermogram comprising an endotherm with a maximum at about 308° C.

In one embodiment, provided is a crystalline 4-amino-2-(2,6-dioxopiperidine-3-yl)isoindoline-1,3-dione dihydrate, having a differential scanning calorimetry thermogram comprising an endotherm with a maximum at about 309° C.

Figure 3:
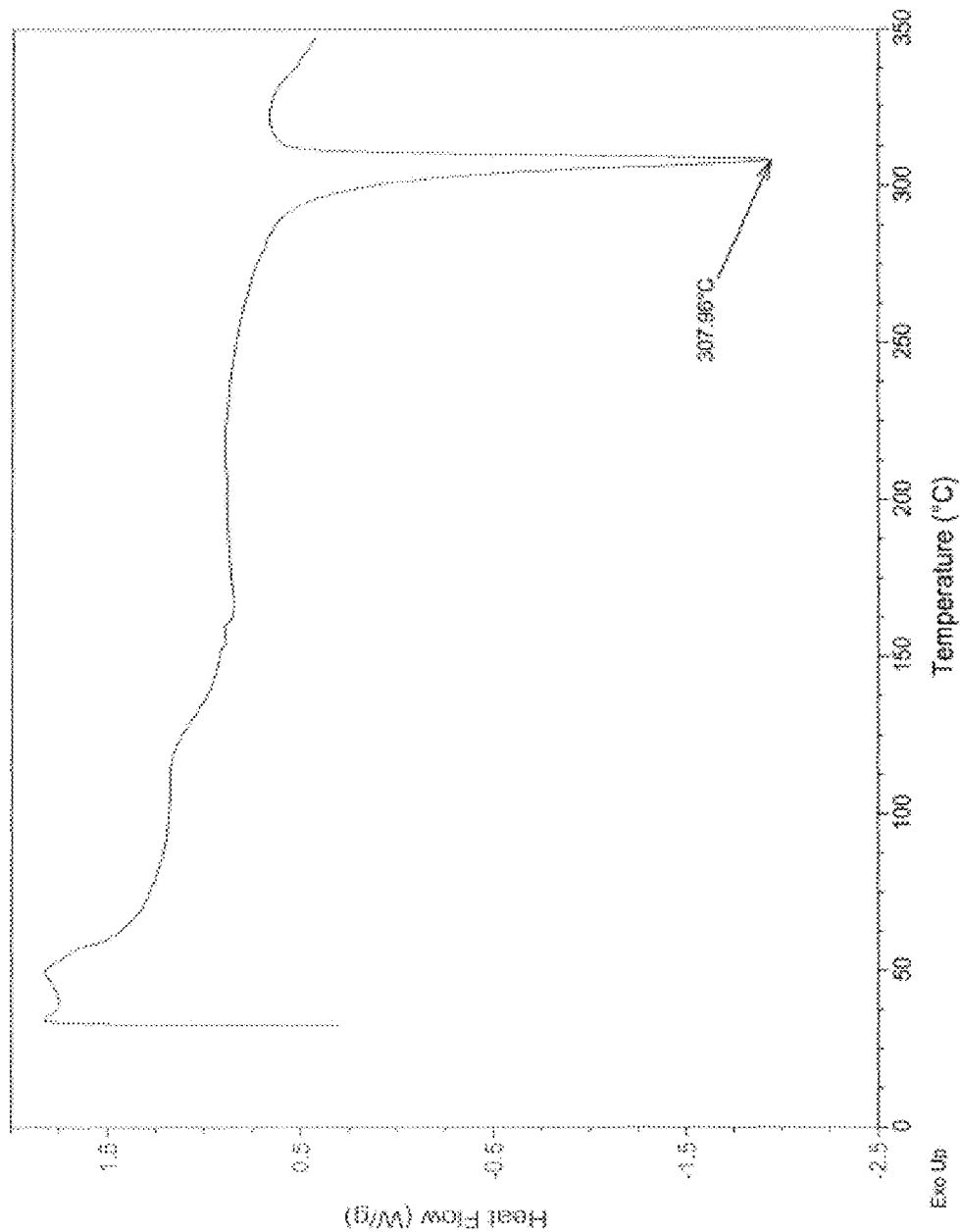
FIG. 3 provides a representative differential scanning calorimetry (DSC) thermogram of crystalline 4-amino-2-(2,6-dioxopiperidine-3-yl)isoindoline-1,3-dione dihydrate.

In one embodiment, provided is a crystalline 4-amino-2-(2,6-dioxopiperidine-3-yl)isoindoline-1,3-dione dihydrate having a differential scanning calorimetry thermogram corresponding to the representative differential scanning calorimetry thermograms depicted in FIG. 3.

Figure 4:
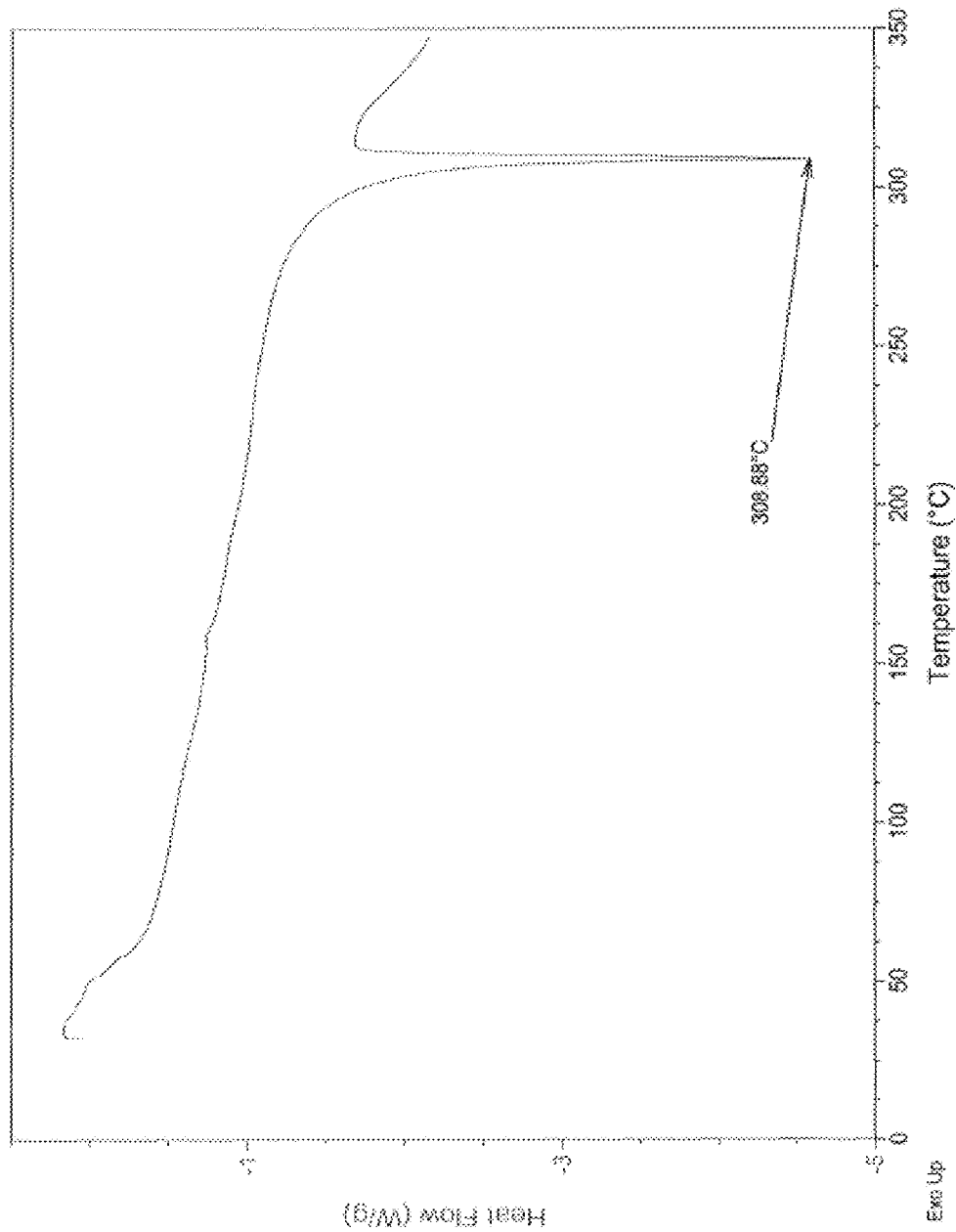
FIG. 4 provides a representative differential scanning calorimetry (DSC) thermogram of crystalline 4-amino-2-(2,6-dioxopiperidine-3-yl)isoindoline-1,3-dione dihydrate.

In one embodiment, provided is a crystalline 4-amino-2-(2,6-dioxopiperidine-3-yl)isoindoline-1,3-dione dihydrate having a differential scanning calorimetry thermogram corresponding to the representative differential scanning calorimetry thermograms depicted in FIG. 4.

In one embodiment, provided is a crystalline 4-amino-2-(2,6-dioxopiperidine-3-yl)isoindoline-1,3-dione dihydrate having approximately 11.6% of water by mass.

In one embodiment, provided is a crystalline 4-amino-2-(2,6-dioxopiperidine-3-yl)isoindoline-1,3-dione dihydrate having a thermogravimetric analysis thermogram comprising a weight loss of about 10.3% when heated from about 30° C. to about 225° C. In one embodiment, provided is a crystalline 4-amino-2-(2,6-dioxopiperidine-3-yl)isoindoline-1,3-dione dihydrate having a thermogravimetric analysis thermogram comprising a weight loss of about 10.1% when heated from about 30° C. to about 225° C. In one embodiment, provided is a crystalline 4-amino-2-(2,6-dioxopiperidine-3-yl)isoindoline-1,3-dione dihydrate having a thermogravimetric analysis thermogram comprising a weight loss of about 10.4% when heated from about 30° C. to about 225° C.

In one embodiment, provided is a crystalline 4-amino-2-(2,6-dioxopiperidine-3-yl)isoindoline-1,3-dione dihydrate having a thermogravimetric analysis thermogram comprising a weight loss of between about 10.1% and about 10.4% when heated from about 30° C. to about 225° C.

Figure 5:
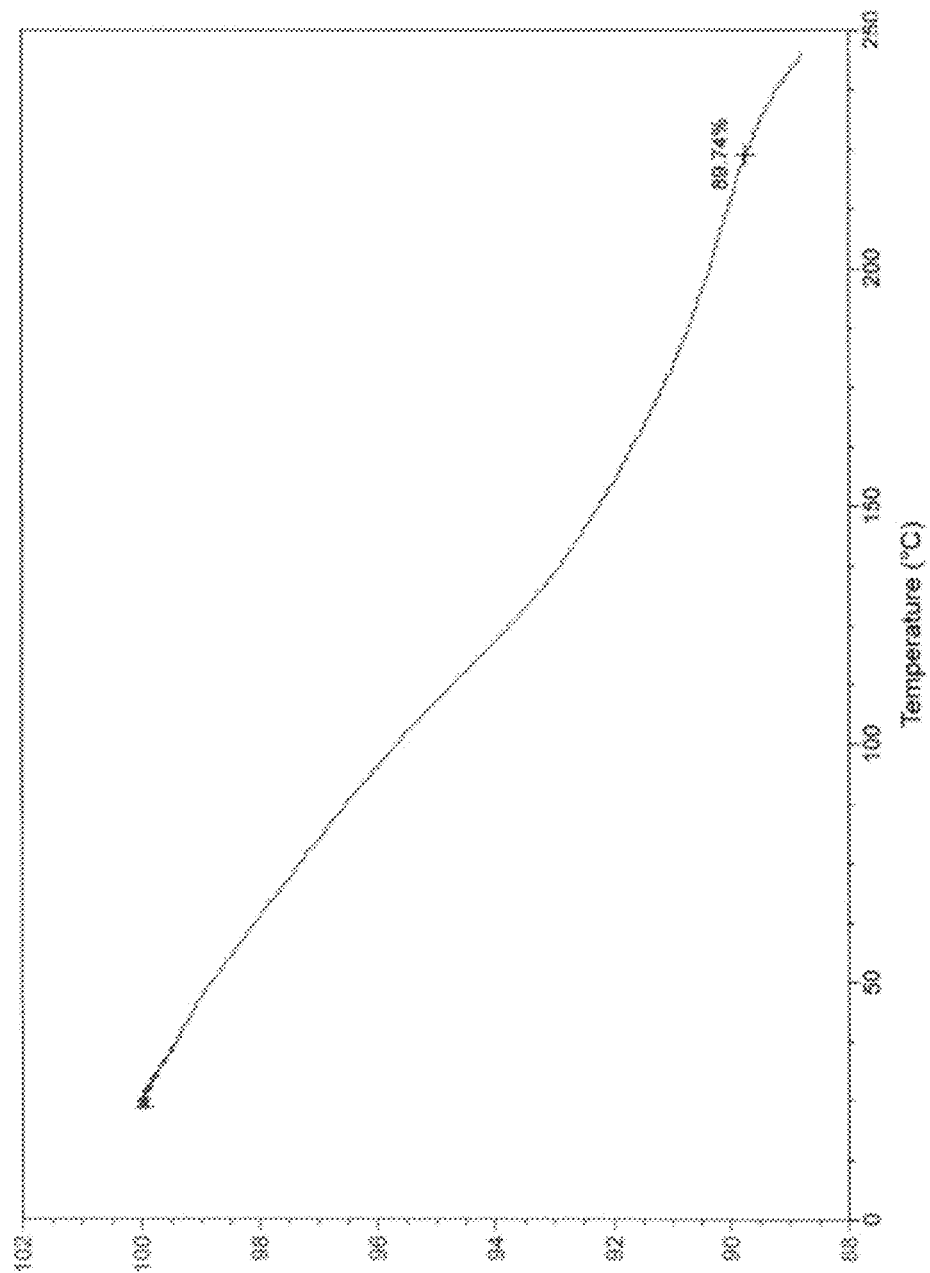
FIG. 5 provides a representative thermogravimetric analysis (TGA) thermogram of crystalline 4-amino-2-(2,6-dioxopiperidine-3-yl)isoindoline-1,3-dione dihydrate.

In one embodiment, provided is a crystalline 4-amino-2-(2,6-dioxopiperidine-3-yl)isoindoline-1,3-dione dihydrate having a thermogravimetric analysis thermogram corresponding to the representative thermogravimetric analysis thermogram depicted in FIG. 5.

Figure 6:
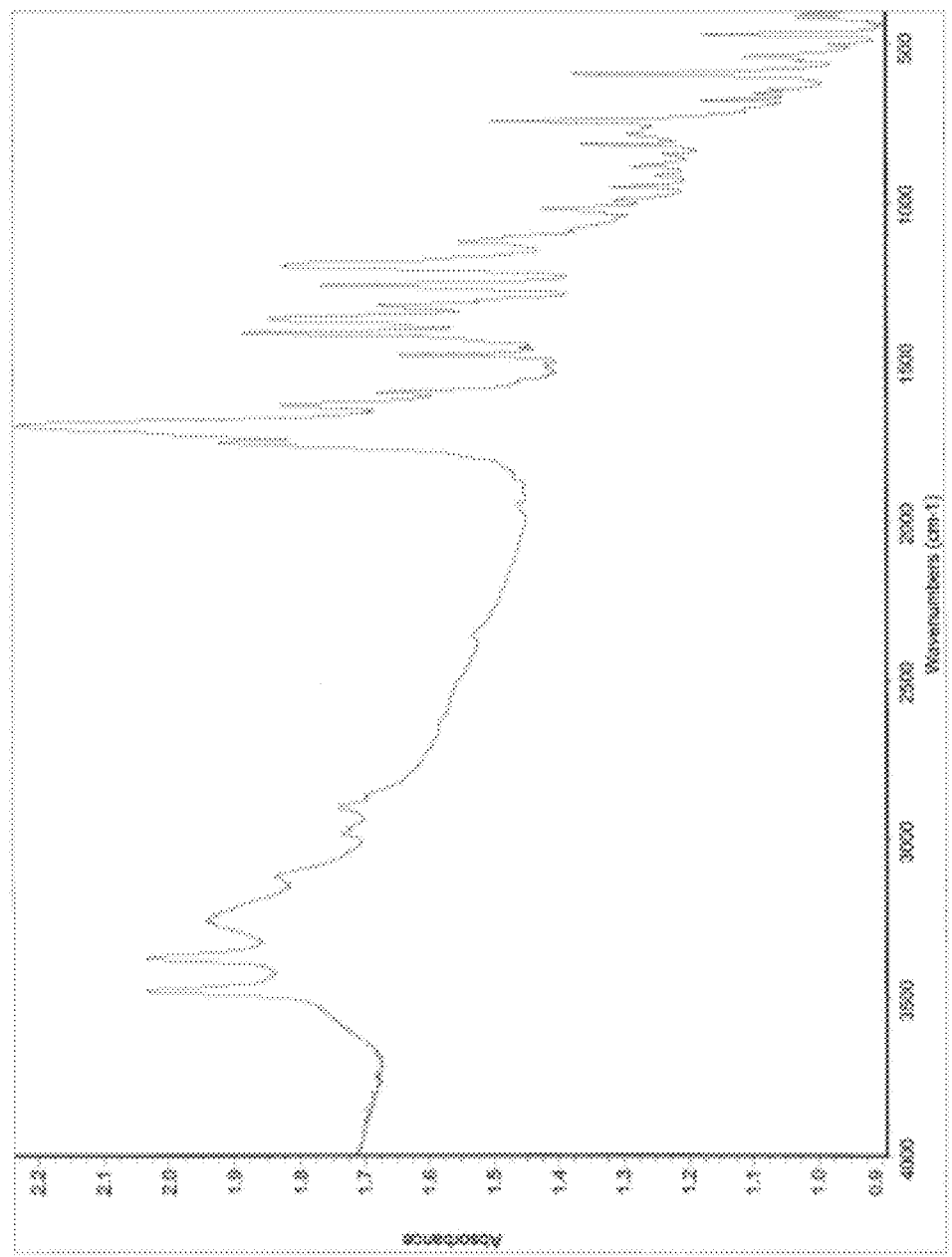
FIG. 6 provides a representative infrared (IR) spectrum of crystalline 4-amino-2-(2,6-dioxopiperidine-3-yl)isoindoline-1,3-dione dihydrate.

In one embodiment, provided is a crystalline 4-amino-2-(2,6-dioxopiperidine-3-yl)isoindoline-1,3-dione dihydrate having an infrared spectrum corresponding to the representative infrared spectrum depicted in FIG. 6.

In one embodiment, provided is a crystalline 4-amino-2-(2,6-dioxopiperidine-3-yl)isoindoline-1,3-dione dihydrate which is substantially physically pure.

In one embodiment, provided is a crystalline 4-amino-2-(2,6-dioxopiperidine-3-yl)isoindoline-1,3-dione dihydrate which is substantially chemically pure.

In one embodiment, provided is a pharmaceutical composition comprising a crystal form of 4-amino-2-(2,6-dioxopiperidine-3-yl)isoindoline-1,3-dione dihydrate.

Pharmaceutical Compositions

Pharmaceutical compositions and single unit dosage forms comprising crystalline 4-amino-2-(2,6-dioxopiperidine-3-yl)isoindoline-1,3-dione dihydrate are provided herein. Also provided herein are methods for preparing pharmaceutical compositions and single unit dosage forms comprising crystalline 4-amino-2-(2,6-dioxopiperidine-3-yl)isoindoline-1,3-dione dihydrate. For example, in certain embodiments, individual dosage forms comprising crystalline 4-amino-2-(2,6-dioxopiperidine-3-yl)isoindoline-1,3-dione dihydrate provided herein or prepared using crystalline 4-amino-2-(2,6-dioxopiperidine-3-yl)isoindoline-1,3-dione dihydrate provided herein may be suitable for oral, mucosal (including rectal, nasal, or vaginal), parenteral (including subcutaneous, intramuscular, bolus injection, intraarterial, or intravenous), sublingual, transdermal, buccal, or topical administration.

In certain embodiments, pharmaceutical compositions and dosage forms provided herein comprise crystalline 4-amino-2-(2,6-dioxopiperidine-3-yl)isoindoline-1,3-dione dihydrate. Certain embodiments herein provide pharmaceutical compositions and dosage forms comprising a crystalline 4-amino-2-(2,6-dioxopiperidine-3-yl)isoindoline-1,3-dione dihydrate, wherein the crystalline 4-amino-2-(2,6-dioxopiperidine-3-yl)isoindoline-1,3-dione dihydrate is substantially pure. Certain embodiments herein provide pharmaceutical compositions and dosage forms comprising a crystalline 4-amino-2-(2,6-dioxopiperidine-3-yl)isoindoline-1,3-dione dihydrate as provided herein, which is substantially free of other crystalline solid forms of 4-amino-2-(2,6-dioxopiperidine-3-yl)isoindoline-1,3-dione and/or amorphous solid forms of 4-amino-2-(2,6-dioxopiperidine-3-yl)isoindoline-1,3-dione. Pharmaceutical compositions and dosage forms provided herein typically also comprise one or more pharmaceutically acceptable excipients, diluents or carriers.

Single unit dosage forms provided herein are suitable for oral or parenteral (e.g., subcutaneous, intravenous, bolus injection, intramuscular, or intraarterial) administration to a patient. Examples of dosage forms include, but are not limited to: tablets; caplets; capsules, such as soft elastic gelatin capsules powders and sterile solids that can be reconstituted to provide liquid dosage forms suitable for parenteral administration to a patient.

Capsules may contain a shell.

The composition, shape, and type of dosage forms provided herein will typically vary depending on their use. A parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

In one embodiment, suitable excipients include mannitol, pregelatinized starch, and sodium stearyl fumarate.

Capsule shells may contain gelatin, titanium dioxide, FD&C blue 2, yellow iron oxide, white ink, and black ink.

Capsule shells may contain gelatin, titanium dioxide, FD&C blue 2, yellow iron oxide, FD&C red 3, and white ink.

Capsule shells may contain gelatin, titanium dioxide, FD&C blue 2, yellow iron oxide, and white ink.

Capsule shells may contain gelatin, titanium dioxide, FD&C blue 1, FD&C blue 2, and white ink.

Like the amounts and types of excipients, the amounts and specific types of active ingredients in a dosage form may differ depending on factors such as, but not limited to, the route by which it is to be administered to patients. However, typical dosage forms provided herein lie within the range of from about 0.1 mg to about 1,000 mg per day, given as a single once-a-day dose in the morning or as divided doses throughout the day. More specifically, the daily dose may be administered twice, three times, or four times daily in equally divided doses. Specifically, a daily dose range may be from about 0.1 mg to about 500 mg per day, more specifically, between about 0.1 mg and about 200 mg per day. A daily dose range may be 1 mg, 2 mg, 3 mg, 4 mg, or 5 mg. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally *Remington's Pharmaceutical Sciences*, 18th ed., Mack Publishing, Easton Pa. (1990).

Typical oral dosage forms provided herein are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101™, AVICEL-PH-103™, AVICEL RC-581M, AVICEL-PH-105™ (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-58™. Suitable anhydrous or low moisture excipients or additives include AVICEL-PH-103™ and Starch 1500 LM™.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

Parenteral Dosage Forms

Parenteral dosage forms can be administered to patients by various routes including, but not limited to, subcutaneous, intravenous (including bolus injection), intramuscular, and intraarterial injection. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herien are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein.

EXAMPLES

Preparation of crystalline 4-amino-2-(2,6-dioxopiperidine-3-yl)isoindoline-1,3-dione dihydrate: 20 mg of pomalidomide Form A (anhydrate) was slurried in a mixture of 20 mL 1,4-dioxane and 5 mL water in a 50 mL round bottom flask. The pomalidomide was completely dissolved at 70° C. with the use of a rotoary evaporator. The temperature was raised to 90° C., and an aspirator vacuum was then applied. Within 10 minutes, the solvent was evaporated and a pale yellow liquid remained in the flask. The flask was cooled to room temperature (ca. 22° C.), and the pale yellow liquid was triturated with 20 mL water. After centrifugation, a pale yellow solid was isolated. The pale yellow solid was dried under a vacuum of 50 torr for three hours. The resulting pale yellow, free flowing powder was taken for analysis.

Karl-Fischer titration revealed the crystalline 4-amino-2-(2,6-dioxopiperidine-3-yl)isoindoline-1,3-dione dihydrate contained 10.5% water.

XRPD data for the crystalline 4-amino-2-(2,6-dioxopiperidine-3-yl)isoindoline-1,3-dione dihydrate is shown below in Table 1.

Scan Type: Normal

Start Angle: 3 deg

Stop Angle: 35 deg.

Num Points: 1601

Step Size: 0.02 deg.

Datafile Res: 1600

Scan Rate: 0.000667

Scan Mode: Step

Wavelength: 1.540562 Å

| | |
|---|---|
| Tube divergent | 2.00 mm |
| Tube scatter | 4.00 mm |
| Detector scatter | 0.50 mm |
| Detector reflection | 0.30 mm |

TABLE 1

XRPD data for crystalline 4-amino-2-(2,6-dioxopiperidine-3-yl)isoindoline-1,3-dione dihydrate.

| Peaks: (Deg.) | Position (Dsp.) | Intensity (cps) | Rel. Int. % |
|---|---|---|---|
| 11.9 | 7.4363 | 244.44 | 39.80 |
| 12.7 | 6.9710 | 181.48 | 29.55 |
| 13.9 | 6.3741 | 385.77 | 62.80 |
| 16.6 | 5.3250 | 367.50 | 59.83 |
| 16.9 | 5.2498 | 356.33 | 58.01 |
| 18.1 | 4.8975 | 235.19 | 38.29 |
| 22.6 | 3.9263 | 174.07 | 28.34 |
| 23.9 | 3.7223 | 251.85 | 41.00 |
| 24.8 | 3.5859 | 231.48 | 37.69 |
| 25.5 | 3.4876 | 614.25 | 100.00 |
| 27.8 | 3.2080 | 261.11 | 42.51 |
| 28.2 | 3.1628 | 290.35 | 47.27 |
| 31.8 | 2.8142 | 144.44 | 23.52 |

Additional experiments to prepare crystalline 4-amino-2-(2,6-dioxopiperidine-3-yl)isoindoline-1,3-dione dihydrate are listed below.

Preparation of crystalline 4-amino-2-(2,6-dioxopiperidine-3-yl)isoindoline-1,3-dione dihydrate: 20 mg of pomalidomide Form A (anhydrate) was slurried in a mixture of 7 mL acetone, 7 mL isopropanol, and 7 mL water in a 50 mL round bottom flask. The pomalidomide was completely dissolved at 70° C. with the use of a rotary evaporator. The temperature was raised to 90° C., and an aspirator vacuum was applied. Within 10 minutes, the solvent was evaporated and a pale yellow solid remained in the flask. The pale yellow solid was dried under a vacuum of 50 torr for 0.5 hours followed by further drying at room temperature without vacuum for 12 hours. The resulting pale yellow, free flowing powder was taken for analysis. TGA analysis revealed the crystalline 4-amino-2-(2,6-dioxopiperidine-3-yl)isoindoline-1,3-dione dihydrate contained 10.1% water.

Preparation of crystalline 4-amino-2-(2,6-dioxopiperidine-3-yl)isoindoline-1,3-dione dihydrate: 20 mg of pomalidomide Form A (anhydrate) was slurried in a mixture of 20 mL THF and 5 mL water in a 50 mL round bottom flask. The pomalidomide was completely dissolved at 70° C. with the use of a rotoary evaporator. The temperature was raised to 80° C., and an aspirator vacuum was applied. Within 10 minutes, the solvent was evaporated and a pale yellow solid remained in the flask. The flask was cooled to room temperature (ca. 22° C.), and the pale yellow solid was dried under a vacuum of 50 torr for 1.5 hours. The resulting pale yellow, free flowing powder was taken for analysis. TGA analysis revealed the crystalline 4-amino-2-(2,6-dioxopiperidine-3-yl)isoindoline-1,3-dione dihydrate contained 10.4% water.

Additional Experiments that Did not Result in crystalline 4-amino-2-(2,6-dioxopiperidine-3-yl)isoindoline-1,3-dione dihydrate The following unsuccessful experiments were performed by mixing in a flask Form A of 4-amino-2-(2,6-dioxopiperidine-3-yl)isoindoline-1,3-dione with solvents until dissolution, then the flask was placed on a rotoevapator (fast rotation; vacuum by water aspirator) at various bath temperatures until dryness or until apparent dryness.

Certain experiments produced an oil, which were then triturated as follows: pure HPLC grade water was added to flask containing the oil, and the flask was stirred. If a solid was formed, it was further dried.

TABLE 2

Conditions that did not result in a crystalline dihydrate of 4-amino-2-(2,6-dioxopiperidine-3-yl)isoindoline-1,3-dione.

| Solvent | Co-solvent | Ratio of solvent/co-solvent | Temperature (° C.) | Notes |
|---|---|---|---|---|
| 1,4-dioxane | N/A | | 60 | |
| THF | Water | 10:1 | 60 | Triturated vacuum dried |
| THF | Water | 1:1 | 80 | |
| Ethanol | Water | 1:1 | 80 | 100° C. for 12 hours after initial drying |
| Ethanol | Water | 1:1 | 80 | Dried further for 20 min at 100° C., then 30 min at 150° C. |
| THF | Water | 1:1 | 80 | |
| 1,4-dioxane | Water | 1:1 | 80 | |
| THF | Water | 24:5 | 80 | |
| THF | Water | 23:5 | 80 | |
| 1,4-dioxane | Water | 1:1 | 80 | Triturated, dried at 150° C. for 1 h |
| THF | Water | 95:5 | 65 | |
| Ethanol | Water | 95:5 | 90 | |
| Ethanol | Water | 98:2 | 90 | |
| THF | Water | 9:1 | 85 | |
| Ethanol | THF/Water | 2:1:2 | 60 | |
| Ethanol | THF/Water | 2:1:2 | 95 | |
| Ethanol | THF/Water | 1:6:1 | 95 | |
| Ethanol | THF/Water | 6:4:1 | 95 | |
| Ethanol | THF/Water | 1:2:1 | 95 | |
| 1,4-dioxane | Water | 1:1 | 95 | Triturated |
| 1,4-dioxane | Water | 1:1 | 95 | Triturated, air tried, 45 m in vacuo |
| Ethanol | THF/Water | 3:5:3 | 80 | Air dried 3 h |
| Ethanol | THF/Water | 3:5:3 | 80 | |
| Acetone | i-PrOH/Water | 1:1:1 | 90 | |
| Acetone | i-PrOH/Water | 1:1:1 | 95 | Material was moist |
| Acetone | i-PrOH/Water | 1:1:1 | 95 | Air dried 18 h |
| Acetone | i-PrOH/Water | 1:1:1 | 95 | Air current dried 3 h |
| Acetone | i-PrOH/Water | 1:1:1 | 95 | Air current dried 1 h |
| Acetone | i-PrOH/Water | 1:1:1 | 85 | |
| 1,4-dioxane | Water | 1:1 | 85 | Material was moist |
| THF | Water | 1:1 | 80 | Air dried |
| THF | Water | 1:1 | 80 | Dried in vacuo for 2 h at 200° C. |
| 1,4-dioxane | Water | 1:1 | 90 | Triturated, dried in vacuo 16 h |
| THF | Water | 4:1 | 95 | |
| THF | Water | 4:1 | 80 | |
| THF | Water | 4:1 | 65 | |
| 1,4-dioxane | Water | 1:1 | 95 | |
| 1,4-dioxane | Water | 4:1 | 80 | Oil, triturated, air dried 4 h |
| 1,4-dioxane | Water | 3:1 | 85 | Air dried 3 h |
| 1,4-dioxane | Water | 3:1 | 85 | Dried overnight at room temperature |
| 1,4-dioxane | Water | 3:1 | 85 | Triturated, dried |
| THF | Water | 4:1 | 80 | Air dried 1 h |
| THF | Water | 12:1 | 70 | Air dried |
| THF | Water | 6:1 | 80 | Air dried |

TABLE 2-continued

Conditions that did not result in a crystalline dihydrate of 4-amino-2-(2,6-dioxopiperidine-3-yl)isoindoline-1,3-dione.

| Solvent | Co-solvent | Ratio of solvent/co-solvent | Temperature (° C.) | Notes |
|---|---|---|---|---|
| MeCN | Water | 2:1 | 80 | Material was moist |
| MeCN | Water | 2:1 | 80 | Dried overnight |
| MeCN | Water | 2:1 | 90 | Air dried |
| 1,4-dioxane | Ethanol/THF/Water | 1:1:1:2 | 85 | Air dried |
| 1,4-dioxane | THF/Water | 6:6:1 | 50 | Material was moist |
| 1,4-dioxane | THF/Water | 6:6:1 | 50 | Dried at 90° C. in vacuo |
| 1,4-dioxane | THF/Water | 6:6:1 | 50 | Air dried |
| Acetone | THF/Water | 10:3:3 | 90 | Air dried |
| THF | Water | 25:1 | 60 | Air dried |
| THF | Water | 25:1 | 60 | |
| THF | Water | 20:1 | 70 | |
| THF | Water | 4:1 | 80 | Air dry |
| THF | Water | 10:1 | 65 | Air dry |
| THF | Water | 10:1 | 75 | |
| Acetone | THF/Water | 10:1:1 | 60 | Air dry |
| 1,4-dioxane | Water | 3:1 | 85 | Triturated |
| 1,4-dioxane | Water | 12:1 | 60 | Triturated |

Characterization Methodology

Samples generated as described in the solid form screen were typically analyzed by X-Ray Powder Diffraction (XRPD). XRPD was conducted on a Scintag X2 X-ray powder diffractometer using Cu Kα radiation at 1.54 Å. In general, positions of XRPD peaks are expected to individually vary on a measurement-by-measurement basis by about ±0.2° 2θ. In general, as understood in the art, two XRPD patterns match one another if the characteristic peaks of the first pattern are located at approximately the same positions as the characteristic peaks of the second pattern. As understood in the art, determining whether two XRPD patterns match or whether individual peaks in two XRPD patterns match may require consideration of individual variables and parameters such as, but not limited to, preferred orientation, phase impurities, degree of crystallinity, particle size, variation in diffractometer instrument setup, variation in XRPD data collection parameters, and/or variation in XRPD data processing, among others. The determination of whether two patterns match may be performed by eye and/or by computer analysis. An example of an XRPD pattern collected and analyzed using these methods and parameters is provided herein, e.g., as FIG. 1.

An example of an XRPD pattern collected and analyzed using these methods and parameters is provided herein, e.g., as FIG. 2.

Differential Scanning calorimetry (DSC) analyses were performed on a TA Instruments Q100™. About 5 mg of sample was placed into a tared DSC closed aluminum pan and the weight of the sample was accurately recorded. An example of a DSC thermogram collected and analyzed using these methods and parameters is provided herein, e.g., as FIG. 3.

An example of a DSC thermogram collected and analyzed using these methods and parameters is provided herein, e.g., as FIG. 4.

Thermal Gravimetric Analyses (TGA) were performed on a TA Instruments Q50™ About 10 mg of sample was placed on an open aluminium pan, accurately weighed and loaded into the TGA furnace. An example of a TGA thermogram collected and analyzed using these methods and parameters is provided herein, e.g., as FIG. 5.

Water determination by the Karl Fischer method was performed using a Metrohm 831 KF Coulometer. The sample was dissolved in anhydrous acetone and injected into the titrator.

Infrared spectroscopy was performed using a ThermoNicolet Nexus 670 spectormeter. A sample of ca. 1 mg of the dihydrate in ca. 100 mg KBr. The mixture was then pressed into a pellet, which was used for the IR study. An example of an IR spectrum collected and analyzed using these methods and parameters is provided herein, e.g., as FIG. 6.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

Citation or identification of any reference in this application is not an admission that such reference is available as prior art. The full scope of the disclosure is better understood with reference to the appended claims.

The invention claimed is:

1. Crystalline 4-amino-2-(2,6-dioxopiperidine-3-yl)isoindoline-1,3-dione dihydrate, having an X-ray powder diffraction pattern comprising peaks at 13.9, 16.6, and 25.5 degrees 2θ±0.2 degrees 2θ, which is substantially physically pure.

2. The dihydrate of claim 1 wherein the X-ray powder diffraction pattern further comprises peaks at 11.9, 16.9, and 28.2 degrees 2θ±0.2 degrees 2θ.

3. The dihydrate of claim 1, having an X-ray powder diffraction pattern corresponding to the representative X-ray powder diffraction pattern depicted in FIG. 1.

4. The dihydrate of claim 1, having an X-ray powder diffraction pattern corresponding to the representative X-ray powder diffraction pattern depicted in FIG. 2.

5. The dihydrate of claim 1, having a differential scanning calorimetry thermogram comprising an endotherm with a maximum at about 308° C.

6. The dihydrate of claim 1, having a differential scanning calorimetry thermogram comprising an endotherm with a maximum at about 309° C.

7. The dihydrate of claim 1 having a differential scanning calorimetry thermogram corresponding to the representative differential scanning calorimetry thermogram depicted in FIG. 3.

8. The dihydrate of claim 1 having a differential scanning calorimetry thermogram corresponding to the representative differential scanning calorimetry thermogram depicted in FIG. 4.

9. The dihydrate of claim 1 having about 11.6% of water by mass.

10. The dihydrate of claim 1 having a thermogravimetric analysis thermogram comprising a weight loss of between about 10.1% and about 10.4% when heated from about 30° C. to about 225° C.

11. The dihydrate of claim 1 having a thermogravimetric analysis thermogram corresponding to the representative thermogravimetric analysis thermogram depicted in FIG. 5.

12. The dihydrate of claim 1 having an infrared spectrum corresponding to the representative infrared spectrum depicted in FIG. 6.

* * * * *